(12) United States Patent
Wolff et al.

(10) Patent No.: US 11,059,790 B2
(45) Date of Patent: Jul. 13, 2021

(54) COMPOUNDS, POLYMERS AND COATING FORMULATIONS THAT COMPRISE AT LEAST ONE N-HALAMINE PRECURSOR, A CATIONIC CENTER AND A COATING INCORPORATION GROUP

(71) Applicant: UNIVERSITY OF MANITOBA, Winnipeg (CA)

(72) Inventors: Zachary J. Wolff, Winnipeg (CA); Sadegh Ghanbar, Winnipeg (CA); Dominic Tessier, Longueuil (CA); Chenxi Ning, Winnipeg (CA); Jonathan van Leeuwen, Winnipeg (CA); Marcelo Dubiel, Winnipeg (CA); Gurmeet Singh Bindra, Winnipeg (CA); Song Liu, Winnipeg (CA)

(73) Assignee: University of Manitoba, Winnipeg (CA)

( * ) Notice: Subject to any disclaimer, the term of this patent is extended or adjusted under 35 U.S.C. 154(b) by 509 days.

(21) Appl. No.: 15/768,824

(22) PCT Filed: Oct. 14, 2016

(86) PCT No.: PCT/CA2016/051200
§ 371 (c)(1),
(2) Date: Apr. 16, 2018

(87) PCT Pub. No.: WO2017/063091
PCT Pub. Date: Apr. 20, 2017

(65) Prior Publication Data
US 2018/0297957 A1    Oct. 18, 2018

Related U.S. Application Data

(60) Provisional application No. 62/393,757, filed on Sep. 13, 2016, provisional application No. 62/362,460, (Continued)

(51) Int. Cl.
*C07D 233/76* (2006.01)
*C07D 211/46* (2006.01)
(Continued)

(52) U.S. Cl.
CPC .......... *C07D 233/76* (2013.01); *A01N 43/40* (2013.01); *A01N 43/50* (2013.01); *C07D 211/46* (2013.01);
(Continued)

(58) Field of Classification Search
CPC .. C07D 233/76; C07D 233/74; C07D 233/78; C07D 211/46; C07D 211/48;
(Continued)

(56) References Cited

U.S. PATENT DOCUMENTS 4,073,926 A * 2/1978 Sonntag ............... C07D 233/72
514/389
2003/0216581 A1 11/2003 Sun
2004/0204521 A1* 10/2004 Camenzind ............. C08K 5/14
524/90

FOREIGN PATENT DOCUMENTS

EP          3362435 A1    7/2019
WO    2013/173905 A1   11/2013
(Continued)

OTHER PUBLICATIONS

International Search Report issued in corresponding Application No. PCT/CA2016/051200, dated Jan. 18, 2017 (8 pages).
(Continued)

*Primary Examiner* — Vincent Tatesure
(74) *Attorney, Agent, or Firm* — Chamberlain, Hrdlicka, White, Williams & Aughtry

(57) ABSTRACT

The present disclosure relates to a compound that has biocidal activity or is a precursor of a compound with biocidal activity. The compound comprises an N-halamine
(Continued)

precursor, at least one quaternary ammonium and at least one coating-incorporation group (CIG). In some embodiments of the present disclosure, the compound may be incorporated into a coating formulation. The coating formulation comprises the compound and at least one further component. In some embodiments of the present disclosure, the CIG reacts with the further component of the coating formulation to incorporate the compound into the coating formulation. In some embodiments, the coating formulation comprises a polymer. In some embodiments, the CIG of the compound reacts with the further component to incorporate the compound into the polymer of the coating formulation. The coating formulation may be used to coat a substrate. The coated substrate may demonstrate biocidal activity or the potential for increased biocidal activity.

7 Claims, 13 Drawing Sheets

Related U.S. Application Data filed on Jul. 14, 2016, provisional application No. 62/287,729, filed on Jan. 27, 2016, provisional application No. 62/275,534, filed on Jan. 6, 2016, provisional application No. 62/269,014, filed on Dec. 17, 2015, provisional application No. 62/248,909, filed on Oct. 30, 2015, provisional application No. 62/245,415, filed on Oct. 23, 2015, provisional application No. 62/242,725, filed on Oct. 16, 2015.

(51) Int. Cl.

| | | |
|---|---|---|
| *C09D 5/14* | (2006.01) | |
| *C08K 5/3435* | (2006.01) | |
| *C08K 5/3445* | (2006.01) | |
| *C07D 211/58* | (2006.01) | |
| *C07D 233/74* | (2006.01) | |
| *A01N 43/40* | (2006.01) | |
| *A01N 43/50* | (2006.01) | |
| *C07D 233/78* | (2006.01) | |
| *C08K 5/19* | (2006.01) | |
| *C08K 5/00* | (2006.01) | |

(52) U.S. Cl.
CPC .......... *C07D 211/58* (2013.01); *C07D 233/74* (2013.01); *C07D 233/78* (2013.01); *C08K 5/3435* (2013.01); *C08K 5/3445* (2013.01); *C09D 5/14* (2013.01); *C08K 5/0058* (2013.01); *C08K 5/19* (2013.01)

(58) Field of Classification Search
CPC ...... A01N 43/40; A01N 43/50; C08K 5/3435; C08K 5/3445; C09D 5/14
USPC ....................................................... 442/152
See application file for complete search history.

(56) References Cited

FOREIGN PATENT DOCUMENTS

| | | | | |
|---|---|---|---|---|
| WO | WO-2013173905 A1 | * | 11/2013 | ........... A01N 43/647 |
| WO | 2017197518 A1 | | 11/2017 | |
| WO | 2018006175 A1 | | 1/2018 | |
| WO | WO2017063091 A1 | | 11/2018 | |

OTHER PUBLICATIONS

Written Opinion issued in corresponding Application No. PCT/CA2016/051200, dated Jan. 18, 2017 (7 pages).
Franck Hui et al.; "Antimicrobial N-Halamine Polymers and Coatings: A Review of Their Synthesis, Characterization, and Applications"; Biomacromolecules; vol. 14, No. 3; pp. 585-601; 2013 (17 pages).
Alexandra Muñoz-Bonilla et al.; "Polymeric materials with antimicrobial activity"; Progress in Polymer Science; vol. 37; pp. 281-339; 2012 (59 pages).
Felix Siedenbiedel et al.; "Antimicrobial Polymers in Solution and on Surfaces: Overview and Functional Principles"; Polymers; vol. 4; pp. 46-71; 2012 (26 pages).
Office Action issued in corresponding application CA2016051200, dated Jul. 3, 2019. (4 pages).

* cited by examiner

A)

B)

(A)

(B)

COMPOUNDS, POLYMERS AND COATING FORMULATIONS THAT COMPRISE AT LEAST ONE N-HALAMINE PRECURSOR, A CATIONIC CENTER AND A COATING INCORPORATION GROUP

CROSS-REFERENCE TO RELATED APPLICATIONS

This application claims the benefit of U.S. Provisional Application No. 62/242,725, filed Oct. 16, 2015, and of U.S. Provisional Application No. 62/245,415, filed Oct. 23, 2015, and of U.S. Provisional Application No. 62/248,909, filed Oct. 30, 2015, and of U.S. Provisional Application No. 62/269,014, filed Dec. 17, 2015, and of U.S. Provisional Application No. 62/275,534, filed Jan. 6, 2016, and of U.S. Provisional Application No. 62/287,729, filed Jan. 27, 2016, and of U.S. Provisional Application No. 62/362,460, filed Jul. 14, 2016, and of U.S. Provisional Application No. 62/393,757, filed Sep. 13, 2016, the entire disclosures of which are incorporated herein by reference.

TECHNICAL FIELD

This disclosure generally relates to compounds having biocidal properties and/or a potential for increased biocidal properties. This disclosure also relates to coating formulations comprising said compounds. The coating formulations are for coating substrates to provide biocidal properties and/or a potential for increased biocidal properties to the coated substrates. In particular, this disclosure relates to coating formulations with at least one compound that comprises an N-halamine precursor group, at least one cationic center, and a coating-incorporation group.

BACKGROUND

Microorganisms, such as bacteria, archaea, yeast or fungi, can cause disease, spoilage of inventory, process inefficiencies, disruptions of healthy natural environments and infrastructure degradation. More specifically, healthcare-associated infections (HAIs) are a serious and growing challenge to health care systems around the world. HAIs cause over 100,000 deaths annually and have become the $3^{rd}$ leading cause of death in Canada. It is estimated that in any given year, HAIs directly cost the United States healthcare system between about $30B and about $45B. Added to this challenge is the increasing prevalence of microorganisms that are resistant to currently available antimicrobial intervention products and processes, including preventative approaches (disinfectants used to control environmental contamination) and reactive approaches (remedies including the use of antibiotics). Therefore, it is necessary to deploy biocidal technologies in various environments as a strategy for controlling unwanted levels or types of micro-organisms.

A common approach for disinfecting of both hard and soft surfaces is the use of liquid disinfectants. Selection of a suitable disinfectant for any given application is dependent upon the environment where the disinfectant will be applied. Selection criteria include the types of micro-organisms targeted, contact time for the disinfectant, level of toxicity tolerable in each application, cleanliness (or lack thereof) of the surface to be cleaned, sensitivity of the surface materials to oxidization (i.e., leading to corrosion of the substrate), the presence or absence of biofilms, the amount of organic load present on substrate surfaces, and local regulations that may restrict the use of certain active ingredients within a disinfectant. Some environments are far more challenging to adequately disinfect than others.

It is known to modify soft surfaces, such as textiles, to provide biocidal properties. For example, the antimicrobial properties of silver have been known since at least the 1960s. Specifically, silver nanoparticles possess broad-spectrum antimicrobial activities and exhibit few toxicological side effects. Currently there are commercially available textiles that incorporate silver, for example, there is a LULULEMON® (Lululemon is a registered trademark of Lululemon Athletica Canada Inc.), SILVERSCENT® (Silverscent registered trademark of Lululemon Athletica Inc.) product that incorporates the X-STATIC® (X-static registered trademark of Noble Fiber Technologies, LLC) silver product. Additionally, UNDER ARMOUR® (Under Armour registered trademark of Under Armour, Inc.) markets a Scent Control technology that comprises a blend of at least silver and zinc. The biocidal activity of these silver-incorporated textiles is limited by the amount of silver that is present and available to react with micro-organisms. The amount of silver is finite and may decrease as the textiles are laundered.

It is also known to modify textiles that incorporate polyethylene terephthalate (PET). These modifications may be achieved by forming a surface network of polyacrylamide (PAM) and PET, and then converting immobilized amides within the surface network to N-chloramine. Composite fabrics with such surface networks have been termed PAM-PETs. PAM-PETs have been challenged with different strains of multi-drug resistant bacteria including health-care acquired *Staphylococcus aureus*, an MRSA (isolate #70065); community-acquired *S. aureus*, also an MRSA (isolate #70527); multi-drug-resistant (MDR) ESBL *E. coli* (isolate #70094); MDR *Pseudomonas aeruginosa* (isolate #73104); and *S. aureus* ATCC 25923. The PAM-PET composite fabric demonstrated close to a 6-log reduction of all the tested bacteria. Furthermore, the N-chloramine on the PAM-PET was evaluated. After 29 regeneration cycles, the PAM-PET (active chlorine 306 ppm) was still able to provide 6-log reduction of HA-MRSA (isolate #70527) within 20 minutes of contact.

International patent application number PCT/CA2013/000491 teaches using forming a semi-interpenetrating network upon a PET surface. The network provides at least one alkynyl group for covalently bonding cyclic amide, azido-5, 5-dimethyl-hydantoin (ADMH). This modified PET sample could bring 7-log reductions of both MDR ESBL #70094 and CA-MRSA #70527. PCT/CA/-2013/00491 also teaches linking the ADMH molecule with a short-chain QAC to create N-(2-azidoethyl)-3-(4, 4-dimethyl-2, 5-dioxoimidazolidin-1-yl)-N, N-dimethylpropan-1-aminium chloride (ADPA) and covalently bonding this molecule onto the PET using the Cu (I)-catalyzed azide-alkyne cyclo addition (CuAAC, usually termed as "click chemistry").

However, forming the surface semi-interpenetrating network as taught by PCT/CA/-2013/00491, as used in the first step of modification as a priming process, cannot be easily scaled up to industrially relevant levels. For example, the process requires multiple processing steps as well as the introduction of environmentally unfriendly additives, such as a methanol bath at elevated temperature. Additionally, the process requires UV irradiation to promote crosslinking in a methanol saturated environment, which may cause a safety concern.

SUMMARY

The present disclosure provides compounds having biocidal properties and coating formulations comprising the compounds. In some embodiments of the present disclosure, the compounds comprise, in a first aspect, an N-halamine precursor group, at least one cationic center, and a coating-incorporation group. As will be described, the compounds and coating formulations may provide a shorter processing time to apply coating formulations to substrates while using processes and equipment that are common within the textile and coating industries. The coating formulations of the present disclosure include compounds with biocidal activity, or precursors to compounds with biocidal activity.

Some embodiments of the present disclosure relate to a single-step coating process that is achieved by designing a durable surface coating formulations that can be broadly applied to a variety of substrates. Additionally, the surface coating may have biocidal activity or it may have a potential for biocidal activity when activated with subsequent treatment step. The chemistry of the coating formulations of the present disclosure allow standard industrial processes to be used for applying the coating formulation to a substrate in a minimal amount of time to increase the cost effectiveness of the application process.

Some embodiments of the present disclosure relate to a compound that has biocidal activity or is a precursor of a compound with biocidal activity. The compound comprises an N-halamine precursor, at least one quaternary ammonium and at least one coating-incorporation group (CIG). In some embodiments of the present disclosure, the compound may be incorporated into a coating formulation. The coating formulation comprises the compound and at least one further component. In some embodiments of the present disclosure, the CIG reacts with the further component of the coating formulation to incorporate the compound into the coating formulation. In some embodiments, the coating formulation comprises a polymer. In some embodiments, the CIG of the compound reacts with the further component to incorporate the compound into the polymer of the coating formulation. The coating formulation may be used to coat a substrate. The coated substrate may then demonstrate biocidal activity or the potential for increased biocidal activity.

Another embodiment of the present disclosure relates to a coating formulation that comprises:

at least one further component that is selected from a group that includes at least: acetate polymers, vinyl ester polymers including vinyl acetate polymers, vinyl acetate homopolymers, acrylate polymers including methacrylate polymers, melamines, modified melamines, urethane polymers, polyurethane polymers, aliphatic urethane polymers, polyesters, self-crosslinking polyesters, epoxide polymers including epoxide-ester polymers, fluoropolymers, silicone or silicone derivative polymers, polyethylene, polypropylene, polyvinyl chloride, polyamides, polybutylene, poly(buta-1,3-diene), polysulfone, or combinations thereof; and a compound that may be selected from a group of compounds that have an alkenyl monomer that comprises at least one N-halamine precursor and at least one quaternary ammonium moiety.

In accordance with another embodiment of the present disclosure, a compound is provided that is selected from a group of compounds that have the general formula [I]:

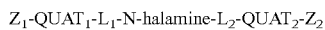

wherein:

the N-halamine is a cyclic halamine or an acyclic N-halamine, when the N-halamine is cyclic then $Z_1$, $QUAT_1$ and $L_1$ are nil (or absent);

$L_1$ and $L_2$ are each independently a linker which can be a $C_1$-$C_{20}$ alkyl, a cyclic aromatic, a non-aromatic ring, ether, ketone, or any other organic linking structure;

$QUAT_1$ has general formula:

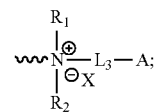

$QUAT_2$ has a general formula:

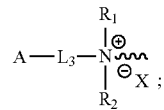

wherein:

$R_1$ and $R_2$ are each independently a $C_1$-$C_6$ alkyl or a $C_1$-$C_6$ alkyl that terminates in a cyclic aromatic group with between 3 and 8 carbons or a cyclic non-aromatic group with between 3 and 8 carbons;

$L_3$ is nil (absent) or a linker which can be one of a $C_1$-$C_{20}$ alkyl; a cyclic aromatic, a non-aromatic ring, ether, ketone, or any other organic linking structure;

$X^-$ is one of $F^-$, $Br^-$, $Cl^-$ or $I^-$;

A is one of $R_3$, cyclic N-halamine, acyclic N-halamine or $-N^+R_4R_5R_6$;

$R_3$ is nil (absent) or one of a $C_1$-$C_{20}$ alkyl; a cyclic aromatic group, a cyclic non-aromatic group, ether, ketone, or any other organic linking structure;

$R_4$ and $R_5$ are each independently a $C_1$-$C_6$ alkyl or a $C_1$-$C_6$ alkyl that terminates in a cyclic aromatic group with between 3 and 8 carbons or a cyclic non-aromatic group with between 3 and 8 carbons;

$R_6$ is nil (absent) or a linker which can be one of a $C_1$-$C_{20}$ alkyl; a cyclic aromatic, a non-aromatic ring, ether, ketone, or any other organic linking structure; and $Z_1$ and $Z_2$ are each independently selected from a group consisting of a direct bond (i.e., $Z_1$ and/or $Z_2$ are absent or nil), a coating-incorporation group (CIG) that is selected from a group consisting of the following functional groups: an alcohol; a primary amine; a secondary amine; a tertiary amine; an ether; an epoxide; a carbonyl group and derivatives thereof such as an acyl, an aldehyde, a ketone, a carboxylic acid, an anhydride, an ester, an amide; an alkyl halide, such as a vinyl chloride, a vinyl fluoride; a vinyl group and derivatives thereof, such as a vinyl acetate and a methyl methacrylate, a vinyl-pyridine, a vinyl-benzylidene; an isocyanate group; a carboxyl group and an associated carboxylate ion; a thiol; a phenol group; an imidazole and $WR_7R_8R_9$, wherein W is selected from the group of N, C, benzene, a cycloaliphatic and another moiety that is capable of bonding with 3 or more further moieties, such further moieties including H, carbon chains or otherwise;

wherein $R_7$, $R_8$ and $R_9$ are each selected from a group comprising: $CH_3$, $CH_2CH_3$, phenyl, $C_3H_6NH_2$, $CH_3H_5$=$CH_2$, $C_3H_4$≡$CH$, $CH_2CH_2R_{13}$,

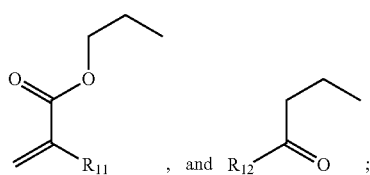

wherein $R_1$ is selected from H, $CH_3$ and CN;

wherein $R_{12}$ is selected from H, OH, $NH_2$, $OCH_3$, and $OCH_2CH_3$; and wherein $R_{13}$ may be selected from any of OH, SH, OCN, CN, NC, SNN and NCS.

In some embodiments of the present disclosure, the CIG may be a branching group that may branch into an aliphatic alkane, alkene or alkyne-chain that is terminated with one or more functional groups.

Another embodiment of the present disclosure relates to a compound that is selected from a group of compounds having one of the general formulas [II] through [XXIII], wherein $X^-$ may be selected from any one of $F^-$, $Br^-$, $Cl^-$ or $I^-$:

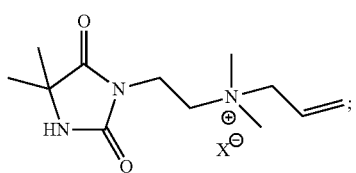
[II]

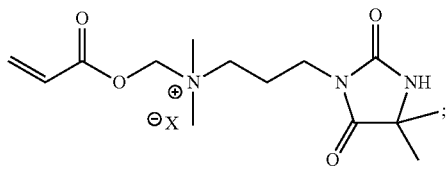
[III]

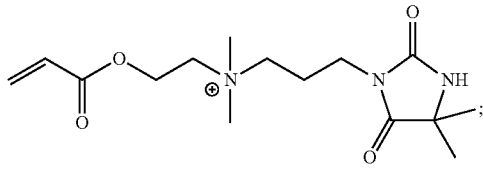
[IV]

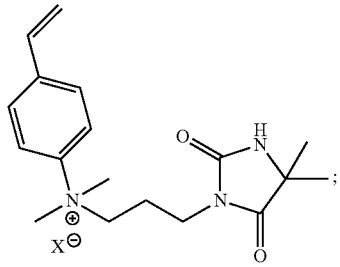
[V]

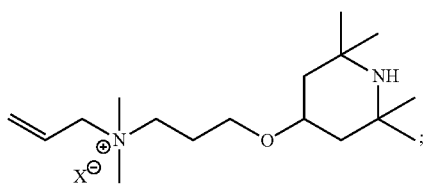
[VI]

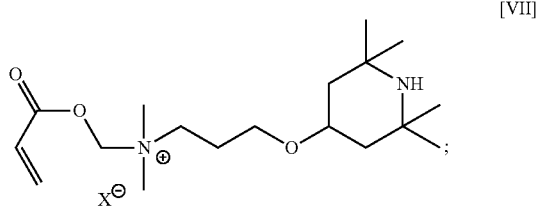
[VII]

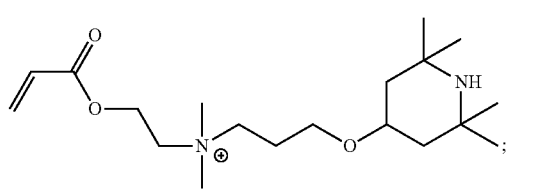
[VIII]

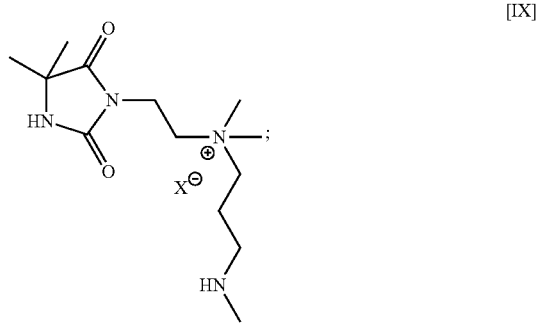
[IX]

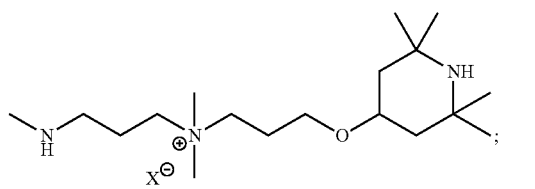
[X]

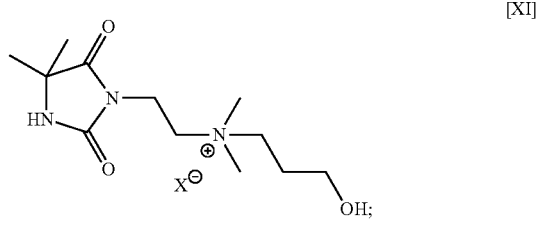
[XI]

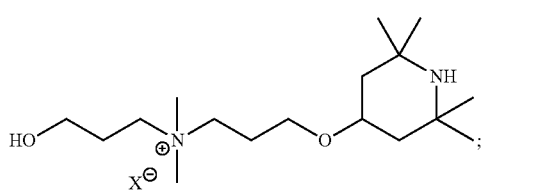
[XII]

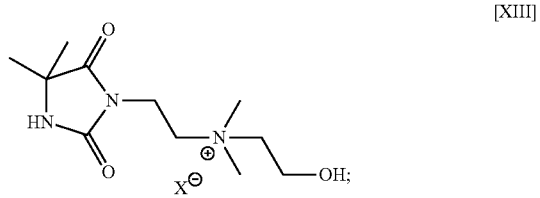
[XIII]

[XIV]
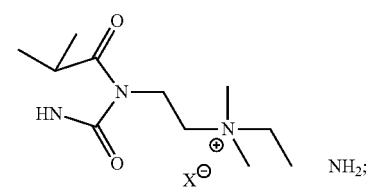

[XV]
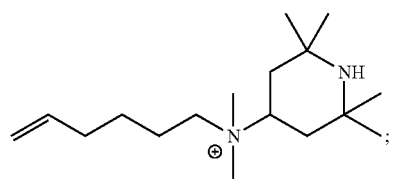

[XVI]
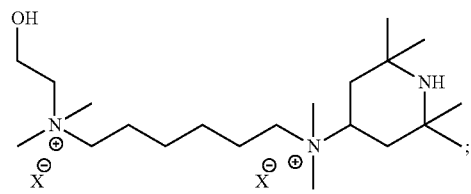

[XVII]
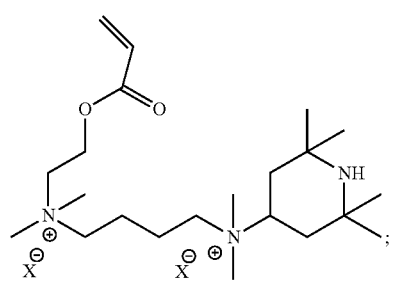

[XVIII]
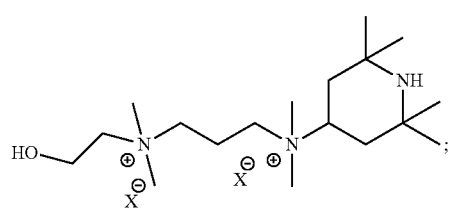

[XIX]
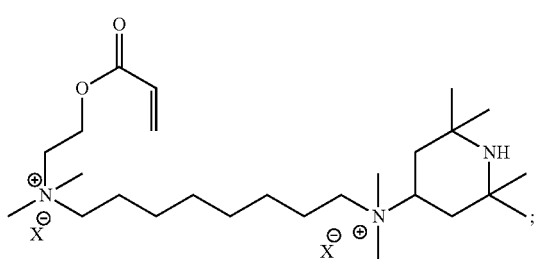

[XX]
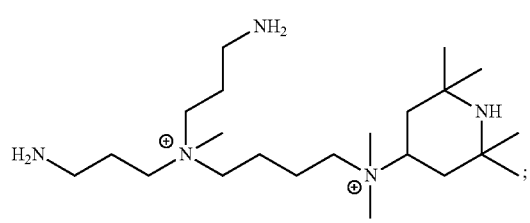

[XXI]
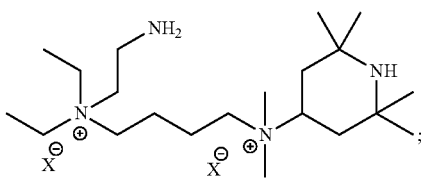

[XXII]
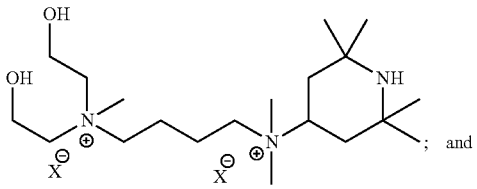
and

[XXIII]
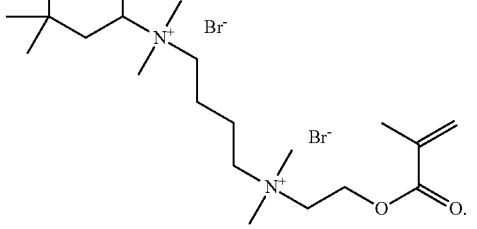

Another embodiment of the present disclosure relates to a process for coating a substrate with a coating formulation. The coating formulation comprises at least one further component that is a polymer selected from a group that includes at least: acetate polymers, vinyl ester polymers including vinyl acetate polymers, vinyl acetate homopolymers, acrylate polymers including methacrylate polymers, melamines, modified melamines, urethane polymers, polyurethane polymers, aliphatic urethane polymers, polyesters, self-crosslinking polyesters, epoxide polymers including epoxide-ester polymers, fluoropolymers, silicone or silicone derivative polymers, polyethylene, polypropylene, polyvinyl chloride, polyamides, polybutylene, poly(buta-1,3-diene), polysulfone, or combinations thereof. The coating formulation also comprises a compound that comprises at least one N-halamine precursor, at least one quaternary ammonium moiety and a CIG. The process comprises the steps of:

coating at least one surface of the substrate with the coating formulation;
drying the coated substrate; and
curing the coated substrate so as to incorporate the CIG of the compound within the coating formulation.

Another embodiment of the present disclosure relates to a substrate comprising at least one surface that is coated with a coating formulation that comprises a polymer selected from a group that includes at least one of: acetate polymers, vinyl ester polymers including vinyl acetate polymers, vinyl acetate homopolymers, acrylate polymers including methacrylate polymers, melamines, modified melamines, urethane polymers, polyurethane polymers, aliphatic urethane polymers, polyesters, self-crosslinking polyesters, epoxide polymers including epoxide-ester polymers, fluoropolymers, silicone or silicone derivative polymers, polyethylene, polypropylene, polyvinyl chloride, polyamides, polybutylene, poly(buta-1,3-diene), polysulfone, or combinations thereof. The coating formulation also comprises a compound that is selected from a group of compounds that comprise an N-halamine precursor, at least one quaternary ammonium moiety and a CIG to incorporate the compound into the polymer of the coating formulation.

BRIEF DESCRIPTION OF THE DRAWINGS

These and other features of this disclosure will become more apparent in the following detailed description in which reference is made to the appended drawings, wherein.

DETAILED DESCRIPTION

Figure 1:
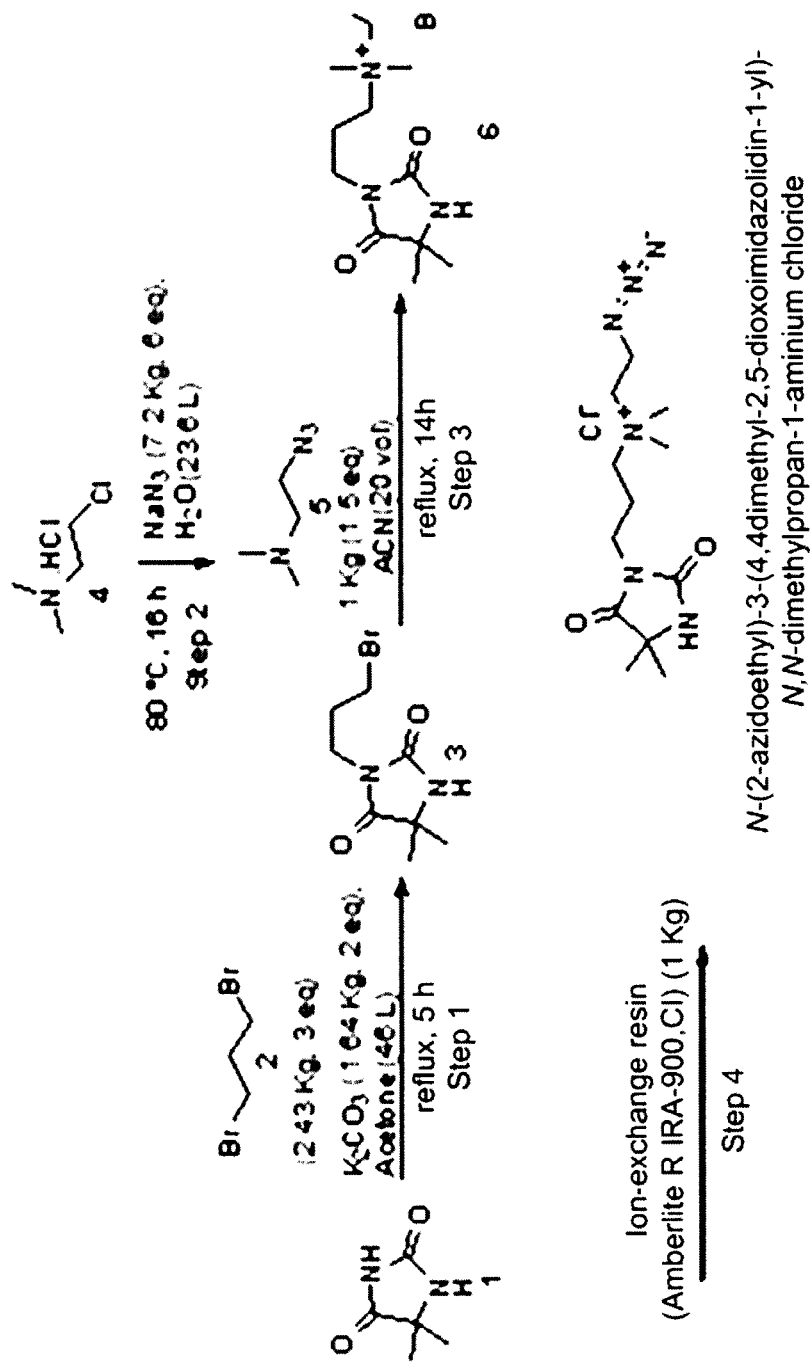
FIG. 1 is a schematic representation of a chemical reaction for synthesizing a compound of the present disclosure.

Some embodiments of the present disclosure relate to one or more compounds that can be incorporated into a coating formulation for coating onto a substrate. After coating, the coated substrate may have biocidal activity or the potential for increased biocidal activity. The potential for increased biocidal activity may be realized by exposing the substrate to one or more additional agents, such as one or more halogens.

Some embodiments of the present disclosure relate to one or more coating formulations that comprise a compound that may be in the form of a monomer. The compound comprises at least (i) one or more cationic centers, (ii) an N-halamine precursor group, and (iii) at least one coating-incorporation group (CIG). In some embodiments of the present disclosure, the CIG may react with another component of the coating formulation or with a component of a substrate or both. In some embodiments of the present disclosure the N-halamine precursor group is at least one of imidazolidine-2, 4-dione (hydantoin); 5, 5-dimethylhydantoin; 4, 4-dimethyl-2-oxazalidione; tetramethyl-2-imidazolidione; 2, 2, 5, 5-tetramethylimidazo-lidin-4-one; a uracil derivative; piperidine or combinations thereof.

In other embodiments of the present disclosure, the N-halamine precursor group may be converted into an N-halamine by a halogenation reaction whereby at least one of the hydrogens present on the N-halamine precursor group is replaced by a halogen atom, such as a chlorine, a bromine or an iodine atom. In some embodiments of the present disclosure, the halogen atom replaces a hydrogen of the N-halamine precursor group that is bonded to a nitrogen atom also of the N-halamine precursor group. In some embodiments of the present disclosure, the replacement reaction may be an addition reaction or some other reaction mechanism.

The CIG may incorporate the compound into the coating formulation or may incorporate the coating formulation onto the substrate, or the CIG may perform both functions. For example, the CIG may link or cure or tether or polymerize the monomer. The CIG may allow the compound to be incorporated into a polymer, including incorporation into the polymer backbone, within various different polymers by different synthesis methods. The different polymers may be synthesized through various synthesis methods, including but not limited to: condensation polymerization; addition polymerization; step-growth polymerization; radical polymerization; chain-growth polymerization; or any combination of these or other polymerization methods through concurrent or subsequent polymer processing or polymerization processes.

In some embodiments of the present disclosure, the compound may be incorporated into a thermoplastic-polymer system that may be synthesized through methods such as those described above or others including additional processing. Additionally, processing of the thermoplastic polymer system may include, but is not limited to: extrusion; co-extrusion; molding; thermoforming; calendaring; compounding; thermoforming or other process may be used to coat or integrate the compound into or onto a base polymer-matrix.

In some embodiments of the present disclosure, the compound may be incorporated into a thermosetting-polymer system or a polymeric precursor thereto that may be processed as described above. Alternatively, processing of the thermoplastic-polymer system and precursors may include, but is not limited to: reaction injection molding or other forming or coating processes, which may or may not involve an addition of a catalyst or other reactive chemistries.

Some embodiments of the present disclosure relate to coating formulations comprising a compound disclosed herein and at least one further component. The compound may be covalently bonded to the at least one further component, or not. In some examples, the coating formulation may further comprise a component that acts as a crosslinking agent.

In some embodiments of the present disclosure, when a CIG of a compound is present it may incorporate the compound into a polymer within a coating formulation. For example when the CIG is:
- a mono-amine, the CIG may be useful for chain growth polymerization into epoxy or polyurethane systems;
- a dual or poly terminated amine, the CIG may allow for curing into epoxy systems through a crosslinking mechanism;
- a dual or poly terminated carboxylic acid, the CIG may allow for curing into epoxy or polyurethane systems through a crosslinking mechanism;
- a hydroxyl group, or a carboxylic acid group, the CIG may be used to tether molecules to epoxide groups present on a surface, as long as a competitive curing process is not taking place at the same time;
- multiple hydroxyl-groups or carboxylic acid groups, the CIG may react into polyurethane polymers through chain growth polymerization and during a cure within a crosslinking reaction;
- a vinyl group or vinyl-acetate group, the CIG may react with various base polymers such as vinyl or silicone-based systems in the presence of a modified melamine crosslinker through a step-growth polymerization process;
- a vinyl acetate group, the CIG may react with ester groups in most any polymer backbone through a step-growth polymerization process;
- a vinyl acetate group, the CIG may homopolymerize to form acrylic or acrylate polymers, or be copolymerized with other moieties to also form vinyl or latex thermoplastic polymers; and
- a vinyl functionality of two or greater in copolymerization with unsaturated polyesters and modified polyesters through condensation polymerization with a glycol and diacid monomer. Forming an unsaturated copolymer;
- a vinyl functionality of two or greater as a cross-linking agent in unsaturated polyester resins and modified polyester resins. Polymer matrix achieved through radical polymerization. Forming a thermoset matrix via chain growth;
- an above-mentioned copolymer with available double or triple bonds utilized as a cross-linking agent in unsaturated polyester resins and modified polyester resins. A polymer matrix may be achieved through radical polymerization. Forming a thermoset matrix via chain growth;
- an above-mentioned copolymer with available double or triple bonds utilized with a cross-linking agent (e.g. styrene) and initiator (such as MEKP). A polymer matrix may be achieved through radical polymerization. Forming a thermoset matrix via chain growth;
- an alkene or vinyl group, which can homopolymerize to form a polyolefin polymer, or be copolymerized with other moieties to form polyethylene, polypropylene, polybutylene, poly(vinyl chloride), or other thermoplastic polymers through an addition polymerization process, or a radical polymerization process; and
- an alkene or vinyl group, which can be co-polymerized with other moieties including but not limited to perfluorocycloalkene, ethylene, vinyl fluoride, vinylidene fluoride (1,1-difluoroethylene), tetrafluoroethylene, chlorotrifluoroethylene, propylene, hexafluoropropylene, perfluoropropylvinylether and perfluoromethylvinylether to form a fluoropolymer through an addition polymerization process, a radical polymerization process, or other polymerization method.

The coating formulation may be coated onto one or more surfaces of the substrate by, for example, a coating process that comprises a step of wetting the substrate surface with a liquid that comprises the coating formulation and a drying step to dry the coated substrate. In some examples, the dried coated-substrate may then be subjected to a subsequent curing step.

Suitable substrates include textiles, metal, metal alloys, polymers, ceramic, glass, natural substances, such as wood, a combinations thereof, and the like. The textiles may be natural, synthetic or combinations thereof.

Definitions

Unless defined otherwise, all technical and scientific terms used herein have the same meaning as commonly understood by one of ordinary skill in the art to which this disclosure belongs.

As used herein, the term "about" refers to an approximately +/−10% variation from a given value. It is to be understood that such a variation is always included in any given value provided herein, whether or not it is specifically referred to.

As used herein, the term "activity" refers to biocidal activity.

As used herein, the term "biocide", refers to a chemical compound, a chemical composition or a chemical formulation that can kill or render harmless one or more microbes.

As used herein, the term "coating formulation", refers to a chemical composition that can be used to coat a substrate, where the chemical composition made may be a mixture of different chemical components that undergo one or more chemical reactions to form a coating upon a substrate.

As used herein, the terms "halo" or "halogen" by themselves or as part of another substituent, have the same meaning as commonly understood by one of ordinary skill in the art, and preferably refer to chlorine, bromine or iodine atom.

As used herein, the terms "microbe" and "microbes" refer to one or more single celled, or multi-cellular, microorganisms exemplified by at least one of bacterium, archaea, yeast or fungi.

The term "N-halamine" as used herein refers to a compound containing one or more nitrogen-halogen covalent bonds that is normally formed by the halogenation of imide, amide or amine groups of a compound. The presence of the halogen renders the compound biocidal. N-halamines, as referred to in the present disclosure, include both cyclic and acyclic N-halamine compounds.

As used herein, the terms "N-halamine precursor" and "N-halamine precursor group" may be used synonymously and can be any N—H, preferably with the absence of an alpha hydrogen, as part of either a cyclic or acyclic organic structure. These functional groups may contain one or more nitrogen-hydrogen bonds that can be converted into a one or more nitrogen-halogen bonds normally formed by the halogenation of imide, amide or amine groups of the functional group. The presence of the halogen may convert an N-halamine precursor into an N-halamine, which may render the functional group biocidal.

As used herein, the terms "quaternary ammonium cation", "quaternary ammonium compound", "quaternary ammonium salt", "QAC", and "quat" may be used interchangeably throughout the present disclosure to refer to ammonium compounds in which four organic groups are linked to a nitrogen atom that produces a positively charged ion (cation) of the structure NR4+.

As used herein, the term "organic linker-group" includes at least the following functional groups phenyl, propane, butane, pentane, hexane, cyclic propane, cyclic butane, cyclic pentane or cyclic hexane.

Some embodiments of the present disclosure relate to compounds that may be selected from a group of compounds having the general formula [I]:

$$Z_1\text{-QUAT}_1\text{-L-N-halamine-L}_2\text{-QUAT}_2\text{-}Z_2 \qquad [I]$$

wherein:

the N-halamine is a cyclic halamine or an acyclic N-halamine, when the N-halamine is cyclic then $Z_1$, $QUAT_1$ and $L_1$ are nil (absent);

$L_1$ and $L_2$ are each independently a linker which can be a $C_1$-$C_{20}$ alkyl, a cyclic aromatic, a non-aromatic ring, ether, ketone, or any other organic linking structure;

$QUAT_1$ has general formula:

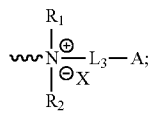

$QUAT_2$ has a general formula:

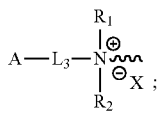

wherein:

$R_1$ and $R_2$ are each independently a $C_1$-$C_6$ alkyl or a $C_1$-$C_6$ alkyl that terminates in a cyclic aromatic group with between 3 and 8 carbons or a cyclic non-aromatic group with between 3 and 8 carbons;

$L_3$ is nil (absent) or a linker which can be one of a $C_1$-$C_{20}$ alkyl; a cyclic aromatic, a non-aromatic ring, ether, ketone, or any other organic linking structure;

$X^-$ is one of $F^-$, $Br^-$, $Cl^-$ or $I^-$;

A is one of $R_3$, cyclic N-halamine, acyclic N-halamine or —$N^+R_4R_5R_6$;

$R_3$ is nil (absent) or one of a $C_1$-$C_{20}$ alkyl; a cyclic aromatic group, a cyclic non-aromatic group, ether, ketone, or any other organic linking structure;

$R_4$ and $R_5$ are each independently a $C_1$-$C_6$ alkyl or a $C_1$-$C_6$ alkyl that terminates in a cyclic aromatic group with between 3 and 8 carbons or a cyclic non-aromatic group with between 3 and 8 carbons;

$R_6$ is nil (absent) or a linker which can be one of a $C_1$-$C_{20}$ alkyl; a cyclic aromatic, a non-aromatic ring, ether, ketone, or any other organic linking structure; and $Z_1$ and $Z_2$ are each independently selected from a group consisting of a direct bond, a coating-incorporation group (CIG) that is selected from a group consisting of the following functional groups: an alcohol; a primary amine; a secondary amine; a tertiary amine; an ether; an epoxide; a carbonyl group and derivatives thereof such as an acyl, an aldehyde, a ketone, a carboxylic acid, an anhydride, an ester, an amide; an alkyl halide, such as a vinyl chloride, a vinyl fluoride; a vinyl group and derivatives thereof, such as a vinyl acetate and a methyl methacrylate, a vinyl-pyridine, a vinyl-benzylidene; an isocyanate group; a carboxyl group and an associated carboxylate ion; a thiol; a phenol group; an imidazole and $WR_7R_8R_9$, wherein W is selected from the group of N, C, benzene, a cycloaliphatic and another moiety that is capable of bonding with 3 or more further moieties, such further moieties including H, carbon chains or otherwise;

wherein $R_7$, $R_8$ and $R_9$ are each selected from a group comprising: $CH_3$, $CH_2CH_3$, phenyl, $C_3H_6NH_2$, $CH_3H_5\!=\!CH_2$, $C_3H_4\!\equiv\!CH$, $CH_2CH_2R_{13}$,

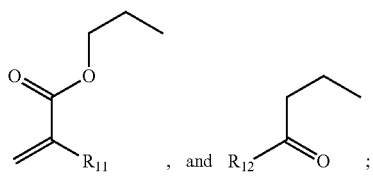

wherein $R_{11}$ is selected from H, $CH_3$ and CN;

wherein $R_{12}$ is selected from H, OH, $NH_2$, $OCH_3$, $OCH_2CH_3$; and wherein $R_{13}$ may be selected from any of OH, SH, OCN, CN, NC, SNN and NCS.

In some embodiments the CIG may be a branching group that may branch into an aliphatic alkane, alkene or alkyne-chain that is terminated with one or more functional groups.

Some embodiments of the present disclosure relate to precursor compounds that are precursor compounds of compounds defined by Formula I, which may be halogenated to produce the above-described N-halamine compounds. Wherein the precursor compounds may or may not have biocidal activity. Accordingly, certain examples relate to precursor compounds having a structure set forth in any one of the above-described embodiments wherein each N-halamine moiety of each halogen substituent is replaced with a hydrogen substituent. Furthermore, each QUAT in the Formula I through Formula XXI above may have different counter ions, such as I In certain further embodiments of the present disclosure, the compounds or precursor compounds are derivatized to allow attachment of the compound or precursor to another compound(s) or surface or substrate or polymer.

In certain further embodiments of the present disclosure, the compounds or precursors disclosed herein may be derivatized to include an azide moiety or an alkynyl group to allow for attachment to another compound(s) or surface or substrate or polymer through "click" chemistry.

In certain further embodiments of the present disclosure, one or more of alkyl groups may be attached to the quaternary ammonium centre in any compound described herein, wherein the alkyl group is derivatized to include a terminal azide or alkynyl moiety.

These examples of compounds, which are not intended to be limited, may comprise further compounds of different general formulae that are generally described in PCT/CA2013/000491, the disclosure of which is incorporated herein by reference.

In some embodiments of the present disclosure the compound is synthesized by the reaction depicted in FIG. 1 and the compound has the general formula (XXV), wherein $X^-$ is one of $Br^-$, $Cl^-$ or $I^-$:

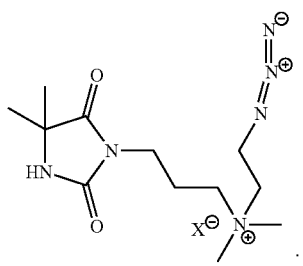

[XXV]

Coating Formulations

Three separate coating formulations referred to herein as AS1 (Coating Formulation 1), AS2 (Coating Formulation 2), and AS3 (Coating Formulation 3) were prepared. Following are details of the constituents of the three formulations, along with specific processing parameters. In all cases, the further components ("C") and H₂O ("B") were mixed, and the compound ("A") was added to the bath. In the following examples, which are not intended to be limiting, the compound used was of the general formula (II) above, which may also be referred to herein as ADPA.

Table 1 provides the mass and % of total mass for the chemical components used to produce the Coating Formulation 1.

TABLE 1

Chemical components used to produce the Coating Formulation 1.

| COATING FORMULATION 1 | AS1 | MASS (G) | % OF TOTAL |
|---|---|---|---|
| A | ADPA [FORMULA XXV] | 2.24 | 0.90 |
| B | H2O | 209.17 | 83.67 |
| C | TRIBUILD DX-164 (PVAC)™ (TRIBUILD is a trademark of Tri-Tex Co, Inc) | 25.73 | 10.29 |
| C | TRICOMEL™ (TRICOMEL is a trademark of Tri-Tex Co, Inc) | 12.86 | 5.15 |
| TOTAL | | 250.00 | 100.00 |
| RATIO OF A: (B + C) (MOL/L) | 0.028 | | |

Table 2 provides the mass and % of total mass for the chemical components used to produce the Coating Formulation 2.

TABLE 2

Chemical components used to produce the Coating Formulation 2.

| COATING FORMULATION 2 | AS2 | MASS (G) | % OF TOTAL |
|---|---|---|---|
| A | ADPA [FORMULA XXV] | 2.24 | 0.90 |
| B | H2O | 209.17 | 83.67 |
| C | TRIBUILD DX-164 (PVAC) | 17.15 | 6.86 |
| C | TRICOMEL | 8.58 | 3.43 |
| C | SANCURE 1004A ® (SANCURE is a registered trademark of Sanncor Industries, Inc.) | 12.86 | 5.15 |
| TOTAL | | 250.00 | 100.00 |
| RATIO OF A TO B + C (MOL/L) | 0.028 | | |

Table 3 provides the mass and % of total mass for the chemical components used to produce the Coating Formulation 3.

TABLE 3

Chemical components used to produce the Coating Formulation 3.

| COATING FORMULATION 3 | AS3 | MASS (G) | % OF TOTAL |
|---|---|---|---|
| A | ADPA [FORMULA XXV] | 1.79 | 0.90 |
| B | H2O | 167.34 | 83.67 |
| C | TRIBUILD DX-164 (PVAC) | 13.72 | 6.86 |
| C | TRICOMEL | 6.86 | 3.43 |
| C | BAYPRET ® NANO-PU (BAYPRET is a registered trademark of Bayer Aktiengesellschaft) | 10.29 | 5.15 |
| TOTAL | | 200.00 | 100.00 |
| RATIO OF A TO B + C (MOL/L) | 0.028 | | |

Figure 3:
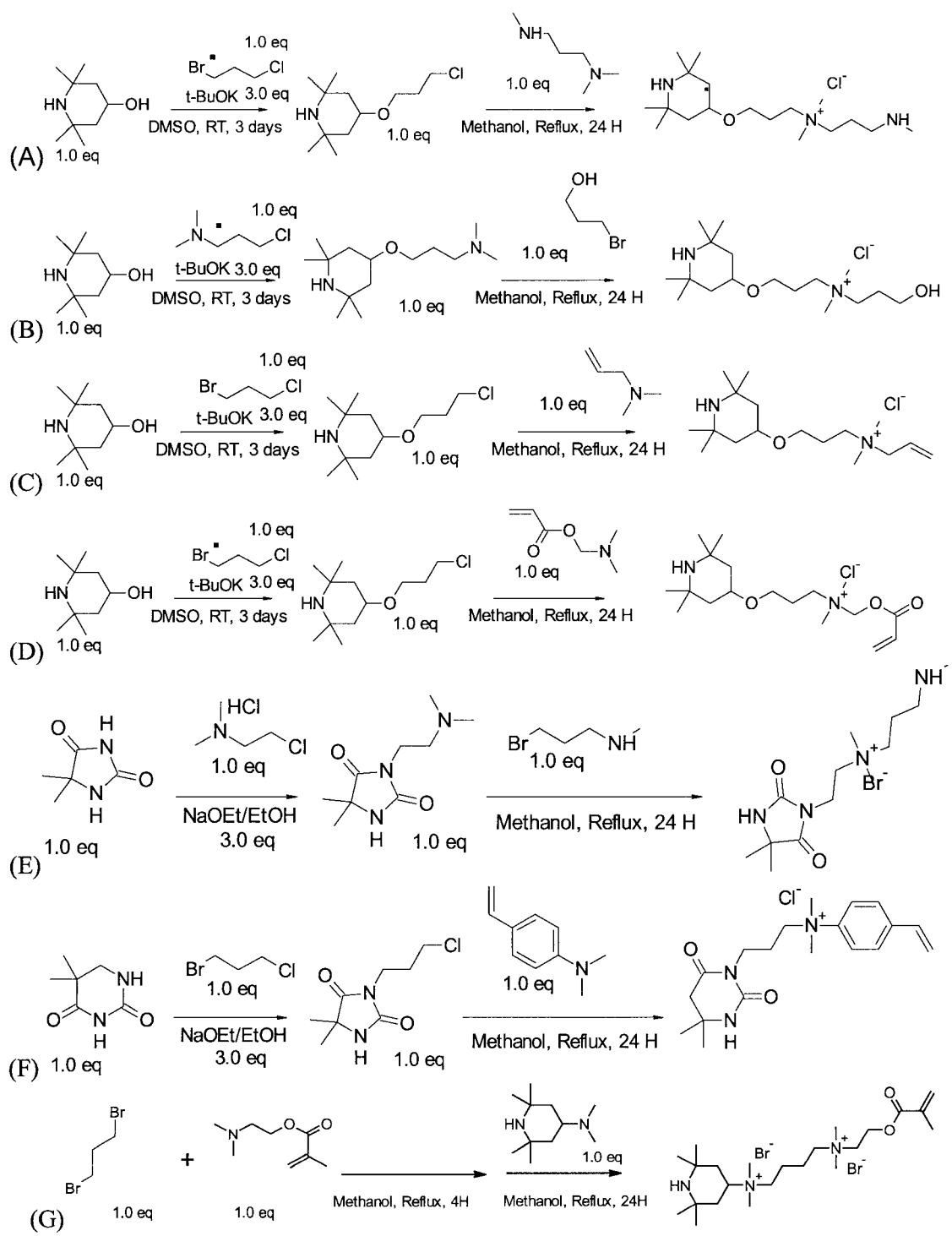
FIG. 3A, FIG. 3B, FIG. 3C, FIG. 3D, FIGS. 3E, 3F and 3G are each schematic representations of chemical reactions for synthesizing further compounds of the present disclosure.

FIG. 3 depicts one coating system 10, which is not intended to be limiting, that may be used to coat a substrate 12 with any of the coating formulations of the present disclosure. The substrate 12 may be flexible, such as a textile, or the substrate 12 may be rigid, such as an article made from any one of: a polymer, a metal, a metal alloy, a synthetic material, a material derived from nature or combinations thereof. When the substrate 12 is a textile coating, the substrate 12 may also be referred to as padding the substrate 12. The coating system 10 comprises a padding mangle 14, a coating tank 16 and a dryer 18. The coating tank 16 may also be referred to as a dip tank. The substrate 12 may proceed through the coating system 10 as a continuous length of material so that one portion of the substrate 12 may be entering the coating system 10 while another portion of the same material may be a coated substrate 12A that is leaving the coating system 10. For example, the substrate 12 may be under tension while moving through the coating system 10. The padding mangle 14 may comprise a first roller 14A, a tank roller 14B and a squeeze roller 14C. The first roller 14A is positioned at an end of the coating system 10 that is opposite to the dryer 18. The first roller 14A may define an entry point of the coating system 10 and the dryer 18 may define an exit point of the coating system 10. As the substrate 12 passes over the first roller 14A, the substrate is pulled into the coating tank 16 by the tank roller 14B. The coating tank 16 holds a coating formulation 20 that will be coated onto the substrate 12 as it passes therethrough. The coating formulation 20 may comprise any one of the coating formulations described herein. The squeeze roller 14C causes the substrate 12 to turn a corner, exit the coating tank 16 and pass through the squeeze roller 14C. The squeeze roller 14C may comprise two rollers that are aligned and spaced apart to allow the substrate 12 to pass through a gap that is defined between the two rollers. The squeeze roller 14C removes excess coating formulation 20, which then falls back into the coating tank 16. Optionally, the distance between the two rollers of the squeeze roller 14C can be changed to increase or decrease a pressure that is applied to the substrate 12 as it passes through the squeeze roller 14C. The pressure applied to the substrate 12 by the squeeze roller 14C may be referred to as a pad pressure. Following the squeeze roller 14C, the substrate 12 then passes through a dryer 18. Optionally, the coating system 20 may also include a curing stage 22, which follows the dryer 18. The curing stage 22 may be a second, downstream section of the dryer 18 or the curing stage 22 may be a separate machine that forms part of the coating system 10.

The coating system 10 may comprise one or more motors (not shown) that turn one or more rollers of the coating padding mangle 14 for pulling the substrate 12, under tension, through the various elements of the coating system 10 at a specified pad speed. Alternatively, the coating system 10 may comprise other motorized rollers (not shown) for pulling the substrate 12 through the coating system 10.

Figure 4:
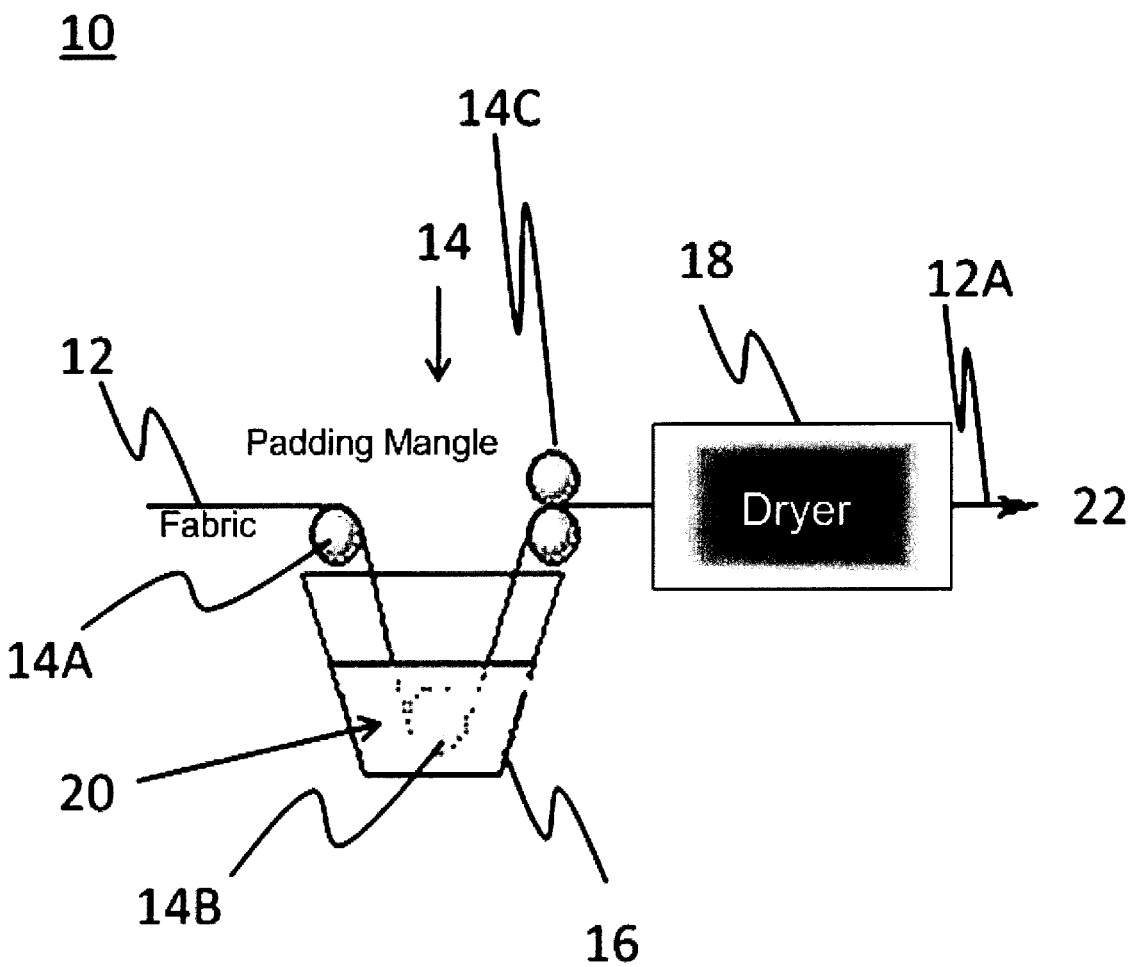
FIG. 4 is a schematic representation of a coating system according to an embodiment of the present disclosure.
Figure 5:
FIG. 5A is a photograph of a further coating system according to the present disclosure.
FIG. 5B is a photograph of an example of processing equipment for use in the coating system depicted in FIG. 4 or FIG. 5A.
Figure 5:
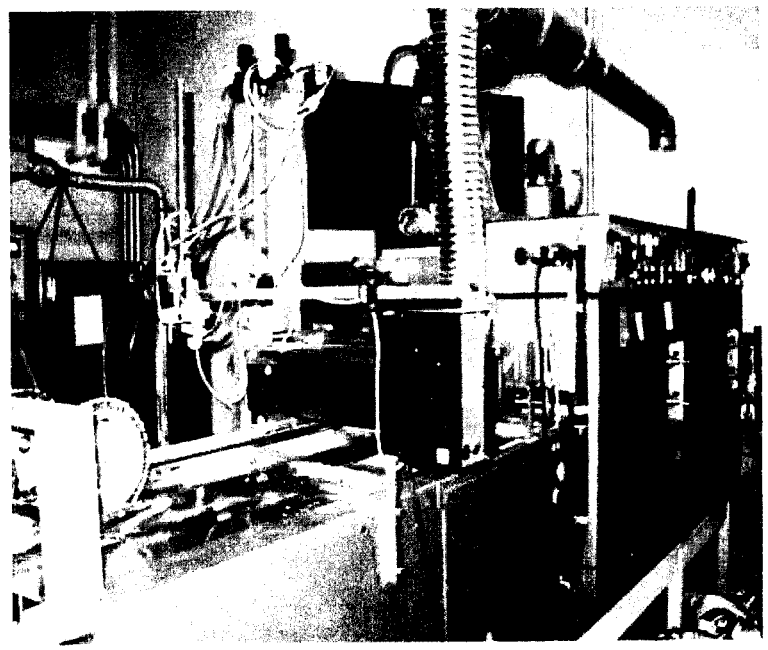

FIG. 4 is a photograph of one example of the coating system 10, the padding mangle 14 and tank 16 is manufactured by Ernst Benz Ag, model KLF HU 500. The rotor and roll size of this model are 4 cm and 10.5 cm, respectively. The maximum volume of the coating tank is about 2 L. Substrate material can be fed at a substantially constant rate of about 0.5 m/min. The size of the substrate 12 samples can be about 30 cm×about 30 cm. The maximum width of substrate 12 that can be accommodated by this apparatus is about 50 cm.

One example of a suitable dryer 18 is manufactured by Ernst Benz Ag, model KFTV 500-DOPPEL. The substrate 12 was passed through the dryer 18 at a rate of about 0.46 m/min. The dryer 18 length may be about 0.96 m and the length of the curing stage 22 may be about an additional 0.96 m.

To coat the substrate 12 with the coating formulation 20, the substrate 12 is subjected to a coating process that comprises a step of pulling the uncoated substrate 12 around the first roller 14A and the tank roller 14B. Next, the uncoated substrate is dipped into the coating tank 16 that contains the coating formulation 20. The substrate 12 is then pulled through the squeeze roller 14C wherein the substrate 12 is squeezed under pressure to remove excess coating formulation 20. The wet pick-up is about 80% to about 100%. The substrate 12 is then pulled into the dryer 18 where it is dried at about 105° C. for about 2 minutes to remove water from the coating formulation 20. The substrate 12 may then move to the curing stage 22 where it is exposed to about 140° C. for about 2 minutes. The higher temperatures of the curing stage 22 may promote the formation of crosslinking within the coating formulation 20, which may increase the durability of the coated substrate 12.

The coating system 10 performs the coating process described above. In particular the equipment that performs the coating process was selected for compatibility with existing industrial processes. Previous methods that were developed to adhere antimicrobial compounds to a substrate 12 were found to rely on multi-stage processes that were likely to introduce enough cost to the manufacturing process to limit the economic feasibility of the disclosure to only certain markets and industries. The coating system 10 and the coating process used in the present method can be directly scaled to industrial-scale textile finishing processes. A typical industrial set-up would have the same process flow as shown in FIG. 3.

The width of the substrate 12 for an industrial coating system 10 is likely to be about 2 meters with a common rate of substrate feeding of about 20 m/min. The dryer 18 and curing section 22 can be scaled to match the scale of the increased feed rate of the substrate 12. The drying process may take place from about 100° C. to about 105° C., and the curing process may occur between about 120° C. to about 170° C.

The Coating Formulations 1, 2 and 3 were used as the coating formulation 20 within the coating system 10 to coat the substrate 12. In one example, the substrate 12 is a textile that is a blend of natural and synthetic fibers, which may be referred to herein as polycotton, that has a ratio of about 65/35 of polyester/cotton (Item Code 7409-CFT, TestFabrics, Inc.). The results obtained by applying the finishing process to the polycotton, which is a synthetic dominated blend, indicates that the coating formulations developed may adhere to other polymer substrates as well.

Table 4 provides the parameters of the coating system 10 for each of the Coating Formulations 1, 2 or 3, with Coating Formulation 3 being used under two different coating parameters.

TABLE 4

Parameters used in the coating system with three coating formulations.

| FORMULATION | COATING FORMULATION 1 | COATING FORMULATION 2 | COATING FORMULATION 3 | COATING FORMULATION 3' |
|---|---|---|---|---|
| PAD SPEED, (m/min) | 0.5 | 0.5 | 0.5 | 0.5 |
| PAD PRESSURE | 5 | 5 | 6.5 | 5 |
| DRYING TEMPERATURE (° C.) | 105 | 105 | 105 | 105 |
| DRYING TIME (mm) | 2 | 2 | 2 | 2 |
| CURING TEMPERTAURE (° C.) | 140 | 140 | 140 | 140 |
| CURING TIME (min) | 2 | 3.5 | 3.5 | 3.5 |

The padding mangle 14 has an arbitrary scale for pad pressure set between 0 and 10. Typically, padding mangles allow the pad pressure to be set using one of PSI, N/m or Kpa as a unit of measure. In the coating system 10, the absolute pad pressure was not measured.

Instead, the pad pressure was adjusted to achieve about 85% wet pickup.

The coated substrates 12A were characterized according to wet pickup %, dry pickup %, and by how much of the coating formulation was added to the substrate 12 as a weight % increase. This final parameter was calculated using the following general formula (IXX):

$$(\% \text{ antimicrobial salt in formulation} * \% \text{ wet pickup})/(100 + \% \text{ dry pickup}) \quad \text{(IXX)}.$$

Three different sample forms of each coated substrate were evaluated: non-chlorinated (AS1, AS2, AS3, AS3'), chlorinated in a single wash cycle (AS1-GCTT-Cl, AS2-

GCTT-Cl, AS3-GCTT-Cl), and chlorinated in 5 wash cycles (AS1-GCTT-5Cl, AS2-GCTT-5Cl, AS3-GCTT-5Cl). The wash cycles were performed according to the AATCC 188-2010 test method, "Colorfastness to Sodium Hypochlorite Bleach in Home Launderings." The wash cycles were conducted to provide data on the amount of active chlorine loading possible with the coating formulations, and to evaluate the durability of the coatings to a simulated life cycle.

Table 5 below provides the wet pick-up, the dry pick-up, the antibacterial salt % measured in some of the coated substrates 12A that were coated with the Coating Formulations 1, 2 or 3 with various degrees of chlorination.

The coating process described above may also be used to adhere a coating to other substrates, such as a polymer film 112. Optionally, a surfactant may be used to provide adequate wettability and spreading of the coating formulation, if desired, for coating various surfaces such as polyethylene terephthalate (PET) fibers, such as polycotton, and PET films.

The further component TRIBUILD DX-164 (Tri-Tex Co, Inc) is a homopolymer of polyvinyl acetate and TRICOMEL 100 (Tri-Tex Co, Inc) is a modified melamine which will crosslink almost any crosslinkable polymer such as carboxylated styrene butadiene, acrylic, polyvinyl acetate, polyvinyl chloride, amino functional silicone, and others. Without being bound by any particular theory, it is postulated that the further components TRIBUILD DX-164 and TRICOMEL 100 can react during the curing process to form a thin film of polymer coating on textile substrates. The thin-film coating formulations may hold embedded antimicrobial compounds or precursors thereof in place. The compounds described herein that are part of a Coating Formulation may be embedded, absorbed or trapped, inside the thin-film polymer coatings. In this physical arrangement, sufficient N-halamine groups may be available to bind, uptake, upload or otherwise bond to a chlorine atom from the local environment of the substrate's surface.

TABLE 5

The wet pick-up, the dry pick-up, the antibacterial salt % of the various of coated substrate 12A that were coated with the three Coating Formulations 1, 2 and 3.

| SAMPLE NAME | QUANTITY | WET PICK-UP %, WET | DRY PICK-UP %, DRY | ANTI-BACTERIAL SALT % AS IN FORMULATION | ANTI-BACTERIAL SALT % AS IN TR. FABRIC (APPROX) |
|---|---|---|---|---|---|
| AS1, AS1-GCTT-CL, AS1-GCTT-5CL | 3X (0, 1, 5 W.) | 80.5-82.7 | 5.3-5.4 | 0.9 | 0.7 |
| AS2, AS2-GCTT-CL, AS2-GCTT-5CL | 3X (0, 1, 5 W.) | 80.8-83.3 | 5.0-5.6 | 0.9 | 0.7 |
| AS3, AS3-GCTT-CL, AS3-GCTT-5CL | 3X (0, 1, 5 W.) | 67.7-68.3 | 3.1-3.2 | 0.9 | 0.6 |
| AS3', AS3'-GCTT-CL, AS3'-GCTT-5CL | 3X (0, 1, 5 W.) | 81.9-82.5 | 4.3-4.4 | 0.9 | 0.7 |

Figure 6:
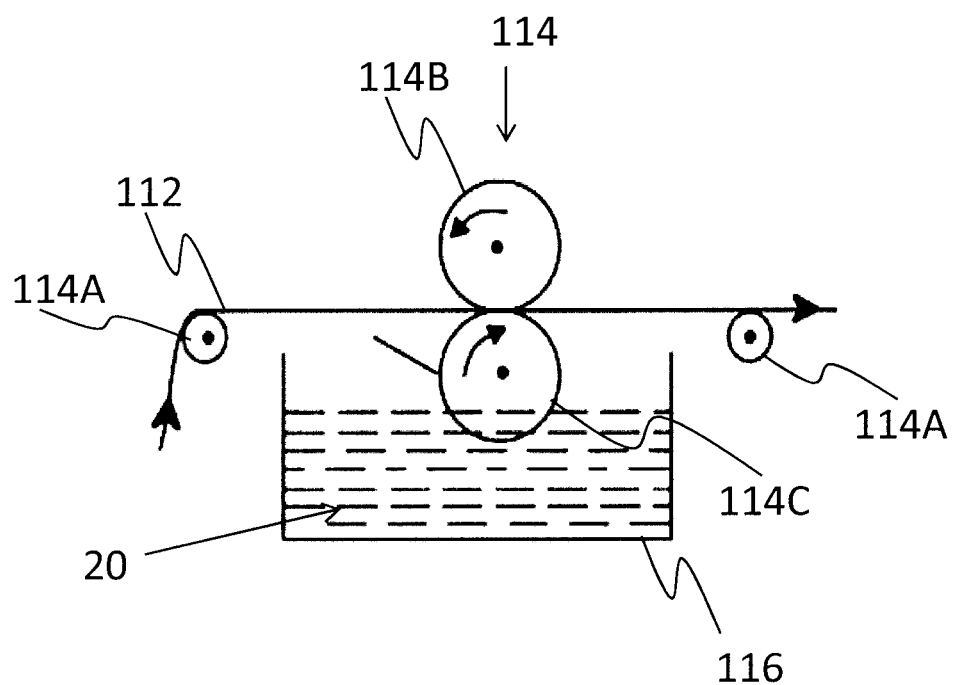
FIG. 6 is a schematic representation of another example of a coating system.

FIG. 6 depicts an example of a coating system 100 that may be suitable for coating a polymer film 112. The coating system 100 comprises a set of one or more rollers 114 and a coating tank 116. The set of rollers may include at least one supporting rollers 114A, an upper roller 114B and a lower roller 114C. The supporting rollers 114A support the polymer film 112 as it moves between the upper roller 114B and the lower roller 114C, which are positioned vertically opposite to each other. Optionally, one or more of the support rollers 114A, the upper roller 114B and the lower roller 114C may be motorized to move the polymer film 112 through the coating system 100. Rotation of the upper and lower rollers 114B, 114C causes the lower roller 114C to dip into and apply the coating formulation 20 to a lower surface of the polymer film 112. As the polymer film 112 passes between the upper and lower rollers 114B, 114C, a compressive force is applied to the polymer film 112, which removes any undesired coating formulation 20 from the coated surface of the polymer film 112. The polymer film 112 then moves along the supporting rollers 114C to a dryer and, optionally, to a curing stage. The dryer and curing stage of system 100 may be similar to those described above for the coating system 10, or not. In one example, the coating system 100 may be similar to, or the same as, a kiss-roll system that is used for finishing membranes.

The further components RayCryl 1853 and RayFlex 683 are polyesters formed from the polymerization of acrylate esters. These further components have a good film-forming property and can adhere strongly to textile substrates. According to the technical notes of RayCryl 1853, this acrylic polymer may also self-crosslink to form a durable film coating.

The Coating Formulations 1, 2 and 3 were designed to covalently bond to polymer substrates. Multiple investigations have shown that the compound of Formula II may not be well-suited to physical incorporation into polymer matrixes due to its solubility in water, which is unlike most antimicrobial agents. Also, the compound is not intended to act as a leaching agent and, therefore, the coating process should permanently adhere the compound to the substrate 12. Typically, surface modification processes (a.k.a. priming) have previously been necessary to form covalent bonds between the compound and the substrate 12. The binding agents selected for the Coating Formulations 1, 2 and 3 are useful as they may form a crosslinked thin-film polymer to physically incorporate or trap the molecular structure of the N-halamine and/or QUAT onto any surface. This allows the compound to be applied to a substrate 12 in a cost-effective manner, yet still provide biocidal activity or the potential for biocidal activity. Other research regarding physical incorporation of the compounds into polymers may have failed because the water solubility of the antimicrobial compounds has led to the agent dissolving out of the matrix when exposed to solvents such as water. Efficacy and durability data for the coating formulations in the AS series samples are provided below. The coating formulations and processes of the present disclosure may demonstrate how to reduce the finishing treatment from multiple processing steps requiring several hours to complete and hazardous working conditions, to a simpler, safer coating process that requires only minutes to perform.

Figure 2:
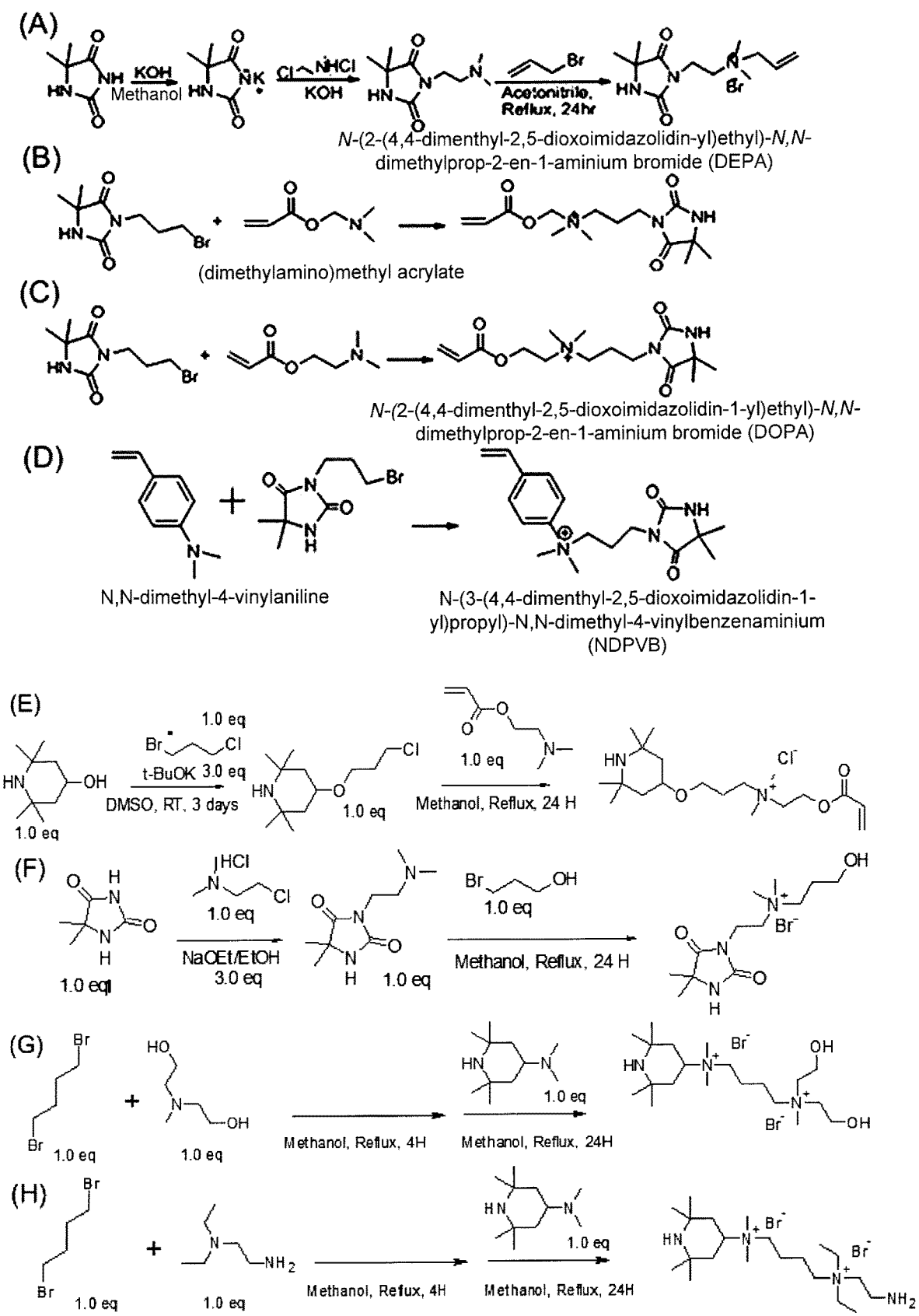
FIG. 2A, FIG. 2B, FIG. 2C, FIG. 2D, FIGS. 2E, 2F, 2G and 2H are each schematic representations of chemical reactions for synthesizing further compounds of the present disclosure.

FIG. 2 and FIG. 3 both depict example chemical reactions for synthesizing examples of a compound, which may also be referred to herein as a monomer or monomer compound.

These examples of compounds may comprise an N-halamine, at least one quaternary ammonium moiety and a CIG. Certain further embodiments of the present disclosure are compounds having the following general formulae [II] through to [XXIII]:

Another embodiment of the present disclosure relates to a compound that is selected from a group of compounds that have one of the general formulas [II] through [XXIIA], wherein X⁻ may be selected from any one of F⁻, Br⁻, Cl⁻ or I⁻:

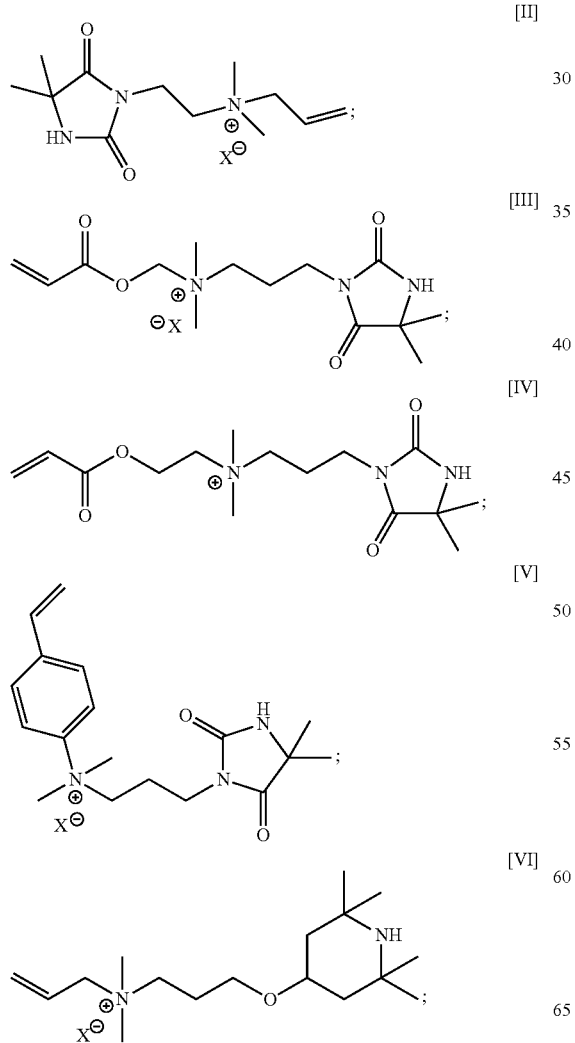

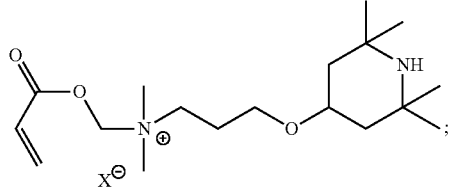

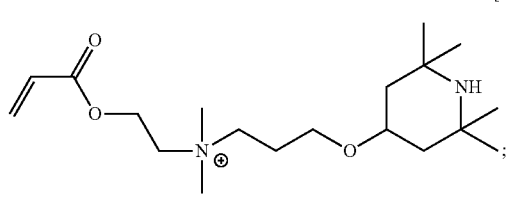

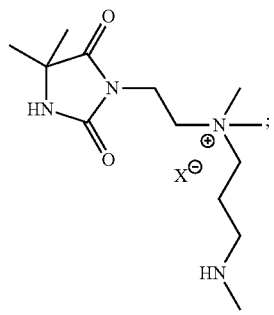

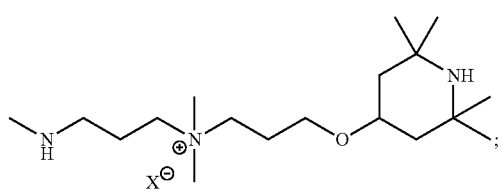

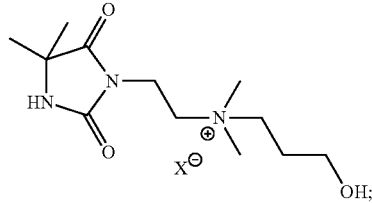

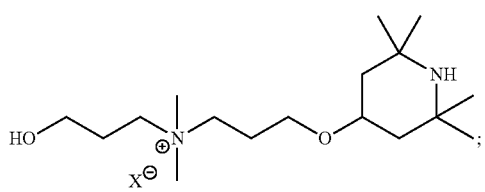

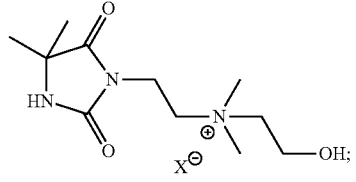

[XIV] 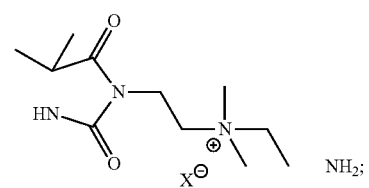

[XV] 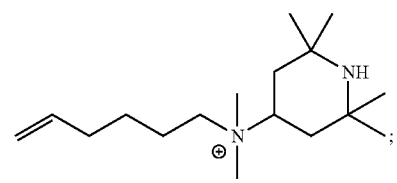

[XVI] 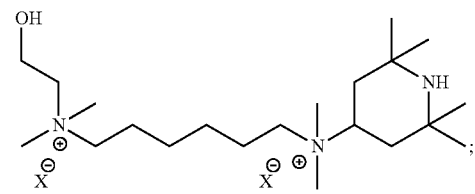

[XVII] 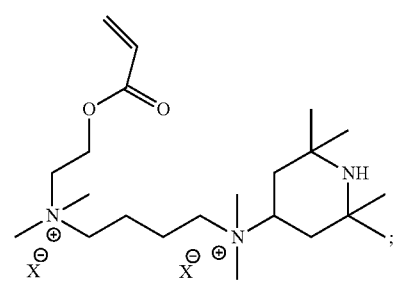

[XVIII] 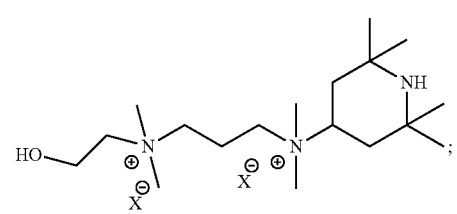

[XIX] 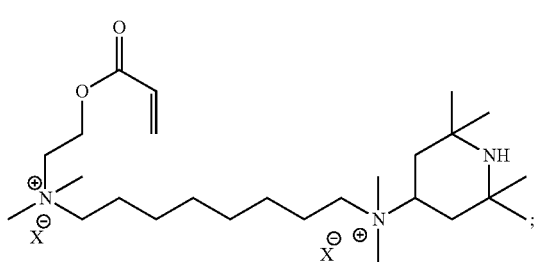

[XX] 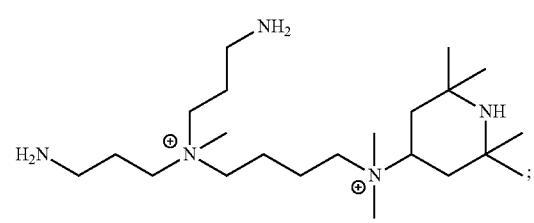

[XXI] 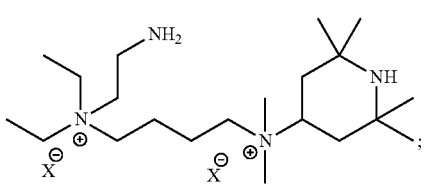

[XXIV] 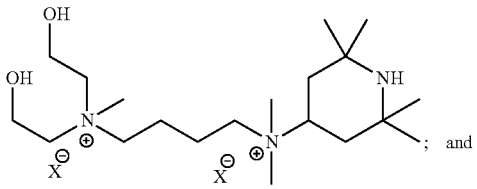
; and

[XXIII] 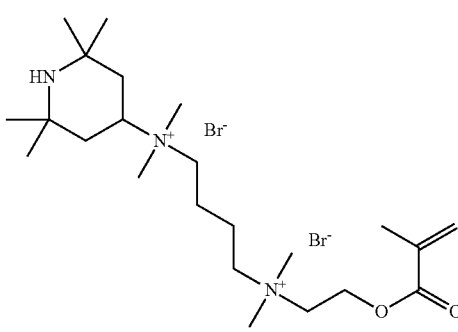

These compounds may also be combined with one or more further components to produce coating formulations. In some embodiments of the present disclosure, the one or more further components may provide heat curing, air curing or photo-curing properties to the coating formulation. In some embodiments of the present disclosure, the coating formulations may comprise a thermoplastic polymer, a precursor or a prepolymer of a thermoplastic polymer, a thermoset polymer, a precursor or a prepolymer of a thermoset polymer or combinations thereof. In another example of the present disclosure, the coating formulations may comprise a polymer that is selected from a group that includes but is not limited to: acetate polymers, vinyl acetate polymers, vinyl acetate homopolymers, melamines, modified melamines, urethane polymers, aliphatic urethane polymers, polyesters, self-crosslinking polyesters, polyaryletherketone polymers, polyether ether ketone polymers or combinations thereof. In further embodiments of the present disclosure, the coating formulations may comprise polyepoxides that may homopolymerize or may polymerize with one or more CIGs, such as but not limited to: polyfunctional amines, acids, acid anhydrides, phenols, alcohols, epoxides and thiols.

In some embodiments of the present disclosure, the coating formulations may comprise a polymer that is selected from a group that includes at least acetate polymers, vinyl ester polymers including vinyl acetate polymers, vinyl acetate homopolymers, acrylate polymers including methacrylate polymers, melamines, modified melamines, urethane polymers, polyurethane polymers, aliphatic urethane polymers, polyesters, self-crosslinking polyesters, epoxide polymers including epoxide-ester polymers, fluoropolymers, silicone or silicone derivative polymers, polyethylene, polypropylene, polyvinyl chloride, polyamides, polybutylene, poly(buta-1,3-diene), polysulfone, or combinations thereof.

During the coating process, the coating formulation can form a thin-film polymer coating that comprises molecules of the compounds disclosed herein that are chemically incorporated into a polymer structure or that are embedded or trapped or otherwise chemically associated with a polymer structure of the coating formulation.

In certain further examples, the further components for the coating formulations may be selected from a group of commercially available chemicals that includes but is not limited to: TRIBUILD DX-164 (Tri-Tex Co, Inc), TRI-COMEL 100 (Tri-Tex Co, Inc), RAYCRYL® 1853 (RAYCRYL is a registered trademark of Specialty Polymers Products, Inc.), RAYFLEX® 683 (RAYFLEX is a registered trademark of Specialty Polymers Products, Inc.), or combinations thereof. Optionally, the coating formulations may also include water. These further components of the coating formulations provide the polymer system within each coating formulation. Each polymer system reacts, in some fashion, with a CIG to incorporate the compounds of the present disclosure into the polymer systems.

Various coating formulations were prepared, which are referred to herein as NC1 (Coating Formulation 4), NC2 (Coating Formulation 5), NC3 (Coating Formulation 6), NC4 (Coating Formulation 7), NC5 (Coating Formulation 8) and NC6 (Coating Formulation 9). Following are details of the constituents of each of the coating formulations, along with specific processing parameters. In all cases, the binding agents ("C") and H$_2$O ("B") were mixed, and then a compound ("A") was added to the bath. In the following examples, which are not intended to be limiting, the coating formulations used was of the general formula (II) above, which herein may also be referred to as DEPA.

Table 6 shows the mass and % of total mass for the chemical components used to produce the Coating Formulation 4.

TABLE 6

Chemical components used to produce the Coating Formulation 4.

| COATING FORMULATION 4 | NC1 | MASS (G) | % OF TOTAL |
|---|---|---|---|
| A | DEPA (FORMULA II) | 1.79 | 0.90 |
| B | H2O | 209.17 | 83.67 |
| C | TRIBUILD DX-164 (PVAC) | 25.73 | 10.29 |
| C | TRICOMEL | 12.86 | 5.15 |
| C | TOTAL | 250.00 | 100.00 |

Table 7 shows the mass and % of total mass for the chemical components used to produce the Coating Formulation 5.

TABLE 7

Chemical components used to produce the Coating Formulation 5.

| COATING FORMULATION 5 | NC2 | MASS (G) | % OF TOTAL |
|---|---|---|---|
| A | DEPA (FORMULA II) | 1.79 | 0.90 |
| B | H2O | 204.02 | 81.61 |
| C | TRIBUILD DX-164 (PVAC) | 25.73 | 10.29 |
| C | TRICOMEL | 18.01 | 7.20 |
| C | TOTAL | 250.00 | 100.00 |

Table 8 shows the mass and % of total mass for the chemical components used to produce the Coating Formulation 6.

TABLE 8

Chemical components used to produce the Coating Formulation 6.

| COATING FORMULATION 6 | NC3 | Mass (g) | % of Total |
|---|---|---|---|
| A | DEPA (FORMULA II) | 1.79 | 0.90 |
| B | H2O | 209.17 | 83.67 |
| C | RayCryl 1853 | 25.73 | 10.29 |
| C | Tricomel | 12.86 | 5.15 |
| C | TOTAL | 250.00 | 100.00 |

Table 9 shows the mass and % of total mass for the chemical components used to produce the Coating Formulation 7.

TABLE 9

Chemical components used to produce the Coating Formulation 7.

| COATING FORMULATION 7 | NC4 | MASS (G) | % OF TOTAL |
|---|---|---|---|
| A | DEPA (FORMULA II) | 1.79 | 0.90 |
| B | H2O | 204.02 | 81.61 |
| C | RAYFLEX 683 | 25.73 | 10.29 |
| C | TRICOMEL | 18.01 | 7.20 |
| C | TOTAL | 250.00 | 100.00 |

Table 10 shows the mass and % of total mass for the chemical components used to produce the Coating Formulation 8.

TABLE 10

Chemical components used to produce the Coating Formulation 8.

| COATING FORMULATION 8 | NC5 | MASS (G) | % OF TOTAL |
|---|---|---|---|
| A | DEPA (FORMULA II) | 1.79 | 0.90 |
| B | H2O | 209.17 | 83.67 |
| C | RAYCRYL 1853 | 38.59 | 15.44 |
| C | TOTAL | 250.00 | 100.00 |

Table 11 shows the mass and % of total mass for the chemical components used to produce the Coating Formulation 9.

TABLE 11

Chemical components used to produce the Coating Formulation 9.

| COATING FORMULATION 9 | NC6 | MASS (G) | % OF TOTAL |
|---|---|---|---|
| A | DEPA (FORMULA II) | 1.79 | 0.90 |
| B | H2O | 209.17 | 83.67 |
| C | RAYFLEX 683 | 38.59 | 15.44 |
| C | TOTAL | 250.00 | 100.00 |

The operational parameters of the coating system 10 for each of the Coating Formulations 4, 5, 6, 7, 8 and 9 were substantially the same with a pad speed of 0.5 meters/minute, a pad pressure of 5 (arbitrary scale between 1 and 10), a drying temperature of 105° C., a drying time of 2 minutes, a curing temperature of 140° C. and a curing time of 2 minutes. The substrate 12 used for these samples was polycotton.

The Coating Formulations 4, 5, 6, 7, 8 and 9 were evaluated in terms of wet and dry pickup, and absolute addition of the biocidal molecule or precursors thereof by weight % addition. The coated samples were either not chlorinated, one-time chlorine washed, or 5-times chlorine washed. These coated samples were evaluated for chlorination propensity and durability of the coating formulations.

The Coating Formulations 3, 4, 5, 6, 7, 8 and 9 following one of the three chlorine washes: non-chlorinated (NC1, NC2, NC3, NC4, NC5, NC6), chlorinated in a one-time chlorine wash cycle (NC1-GCTT-Cl, NC2-GCTT-Cl, NC3-GCTT-Cl, NC4-GCTT-Cl, NC5-GCTT-Cl, NC6-GCTT-Cl), and chlorinated in a 5-times chlorine wash cycle (NC1-GCTT-5Cl, NC2-GCTT-5Cl, NC3-GCTT-5Cl, NC4-GCTT-5Cl, NC5-GCTT-5Cl, NC6-GCTT-5Cl) were evaluated. The different chlorine wash were performed according to the AATCC 188-2010 test method, "Colorfastness to Sodium Hypochlorite Bleach in Home Launderings." The different chlorine wash provided data on the amount of active chlorine loading possible with the example coating formulations, and data relevant to the durability of the example coating formulations.

Table 13 below shows the wet pick-up, the dry pick-up, the antibacterial salt % measured in the various of coated substrates 12A that were coated with the Coating Formulations 4 through 9 with various degrees of chlorination.

TABLE 13

The wet pick-up, the dry pick-up, the antibacterial salt % of the various of coated substrate 12A that were coated with the Coating Formulations 1, 2 and 3.

| SAMPLE NAME | PICK-UP %, WET | PICK-UP %, DRY | ANTI-BACTERIAL SALT % AS IN FORMULATION | ANTI-BACTERIAL SALT % AS IN TR. FABRIC (APPROX) |
|---|---|---|---|---|
| NC1 | 87.5 | 3.8 | 0.9 | 0.7 |
| NC1-GCTT-CL | 88.8 | 4.6 | 0.9 | 0.7 |
| NC1-GCTT-5CL | 87.6 | 4.4 | 0.9 | 0.7 |
| NC2, | 86.5 | 4.4 | 0.9 | 0.7 |
| NC2-GCTT-CL | 86.2 | 4.6 | 0.9 | 0.7 |
| NC2-GCTT-5CL | 87.0 | 4.8 | 0.9 | 0.7 |
| NC3, | 93.2 | 4.4 | 0.9 | 0.8 |
| NC3-GCTT-CL | 88.5 | 4.5 | 0.9 | 0.8 |
| NC4 | 94.1 | 4.0 | 0.9 | 0.8 |
| NC4-GCTT-CL | 89.9 | 4.7 | 0.9 | 0.8 |
| NC5 | 93. | 5.9 | 0.9 | 0.8 |
| NC5-GCTT-CL | 91.3 | 6.8 | 0.9 | 0.8 |
| NC6 | 83.7- | 4.0 | 0.9 | 0.7 |
| NC6-GCTT-CL | 85.6 | 4.9 | 0.9 | 0.7 |
| NC3-GCTT-5CL | 88.6 | 4.4 | 0.9 | 0.8 |
| NC4-GCTT-5CL | 92.2 | 5.1 | 0.9 | 0.8 |
| NC5-GCTT-5CL | 88.5 | 6.5 | 0.9 | 0.7 |
| NC6-GCTT-5CL | 85.6 | 5.1 | 0.9 | 0.7 |

Without being bound by any particular theory, it is postulated that the modified melamine in the TRICOMEL 100 can potentially react with the compounds within the coating formulations either via Michael addition or radical graft polymerization (a radical might be generated on melamine amines upon curing) to bond onto, or within, a thin-film polymer coating, which may result in a more durable coating on the substrate.

Further coating formulations for soft substrates were prepared. The following further coating formulations may be suitable for coating a textile substrate, such as polycotton.

Table 13A provides a summary of the further components of the further coating formulations described further below.

| Product ID | Description |
|---|---|
| Commercial Products | |
| TRIBUILD DX-164 | Water-based emulsion, homopolymer of polyvinyl acetate. |
| TRICOMEL 100 | Water-soluble, modified melamine crosslinker. |
| TRICOSIL ® DMR (TRICOSIL is a registered trademark of Cesare Ragazzi Company) | A silicone-based polymer coating pre-cursor. |
| TRIBUILD MB NPF | Modified polyvinyl acetate copolymer latex, contains no alkyl phenol ethoxylates (APEO) |
| TRICOFRESH LOC | Modified self-catalyzed imidazolidinone, with low levels of fromaldehyde |
| PERMAFRESH ® 600 (PERMAFRESH is a registered trademark of the Sun Chemical Corporation) | Dimethylol dihydroxyl ethyleneurea solution (DMDHEU) |
| Catalyst 531 | Aqueous magnesium chloride solution. Solution is a pH of 1. |
| RayCryl 1853 | High solids acrylic emulsion polymer. Self crosslinking and carboxyl group. APEO free and anionic. |
| Matrix | |
| F2 | Tribuild DX-164 and Tricomel 100 |
| F11 | Trocosil DMR and Trocomel 100 |
| F12 | Trocosil DMR and Tricofresh LOC |
| F13 | Tricosil MB NPF and Tricofresh LOC |
| F14 | Permafresh 600 and Catalyst 531 |
| F15 | RayCryl 1853 |

Table 14 shows the mass and % of total mass for the chemical components used to produce a Coating Formulation 10.

TABLE 14

Chemical components used to produce the Coating Formulation 10.

| COATING FORMULATION 10 | 7409CFT-F2D2P1-1 | | Mass | % |
|---|---|---|---|---|
| A | DEPA (FORMULA II) | g | 0.90 | 0.90 |
| B | H2O | g | 81.60 | 81.60 |
| C | TRIBUILD DX-164 (48% solids) | g | 10.30 | 10.30 |
| C | TRICOMEL 100 (41% solids) | g | 7.20 | 7.20 |
| | TOTAL | g | 100 | 100 |

Table 15 shows the mass and % of total mass for the chemical components used to produce a Coating Formulation 11.

TABLE 15

Chemical components used to produce the Coating Formulation 11.

| COATING FORMULATION 11 | 7409CFT-F2D2P1-2&3 | | Mass | % |
|---|---|---|---|---|
| A | DEPA (FORMULA II) | g | 0.90 | 0.90 |
| B | H2O | g | 90.36 | 90.35 |
| C | TRIBUILD DX-164 (48% solids) | g | 5.15 | 5.15 |
| C | TRICOMEL 100 (41% solids) | g | 3.60 | 3.60 |
| | TOTAL | g | 100 | 100 |

Table 16 shows the mass and % of total mass for the chemical components used to produce a Coating Formulation 12.

TABLE 16

Chemical components used to produce the Coating Formulation 12.

| COATING FORMULATION 12 | 7409CFT-F11D2P1 | | Mass | % |
|---|---|---|---|---|
| A | DEPA (FORMULA II) | g | 0.90 | 0.90 |
| B | H2O | g | 88.90 | 88.90 |
| C | TRICOSIL DMR | g | 3.00 | 3.00 |
| C | TRICOMEL 100 (41% solids) | g | 7.20 | 7.20 |
| | TOTAL | g | 100 | 100 |

Table 17 shows the mass and % of total mass for the chemical components used to produce a Coating Formulation 13.

TABLE 17

Chemical components used to produce the Coating Formulation 13.

| COATING FORMULATION 13 | 7409CFT-F12A1P2 | | Mass | % |
|---|---|---|---|---|
| A | ATH (FORMULA XIV) | g | 1.79 | 1.79 |
| B | H2O | g | 80.21 | 80.21 |
| C | TRICOSIL DMR | g | 3.00 | 3.00 |
| C | TRICOFRESH LOC | g | 15.00 | 15.00 |
| | TOTAL | g | 100 | 100 |

Table 18 shows the mass and % of total mass for the chemical components used to produce a Coating Formulation 14.

TABLE 18

Chemical components used to produce the Coating Formulation 14.

| COATING FORMULATION 14 | 7409CFT-F13A1P2 | | Mass | % |
|---|---|---|---|---|
| A | ATH (FORMULA XIV) | G | 1.79 | 1.79 |
| B | H2O | G | 79.21 | 79.21 |
| C | TRIBUILD MB NPF (55% solids) | g | 4.00 | 4.00 |
| C | TRICOFRESH LOC | g | 15.00 | 15.00 |
| | TOTAL | g | 100 | 100 |

Table 19 shows the mass and % of total mass for the chemical components used to produce a Coating Formulation 15.

TABLE 19

Chemical components used to produce the Coating Formulation 15.

| COATING FORMULATION 15 | 7409CFT-F14D2P1-1 | | Mass | % |
|---|---|---|---|---|
| A | DEPA (FORMULA II) | g | 0.90 | 0.90 |
| B | H2O | g | 91.09 | 91.09 |
| C | Permafresh 600 | g | 5.51 | 5.51 |
| C | Catalyst 531 | g | 2.50 | 2.50 |
| | TOTAL | g | 100 | 100.00 |

Table 20 shows the mass and % of total mass for the chemical components used to produce a Coating Formulation 16.

TABLE 20

Chemical components used to produce the Coating Formulation 16.

| COATING FORMULATION 16 | 7409CFT-F14H1P1-1/2 | | Mass | % |
|---|---|---|---|---|
| A | HTH (Formula XIII) | g | 0.90 | 0.90 |
| B | H2O | g | 91.09 | 91.09 |
| C | Permafresh 600 | g | 5.51 | 5.51 |
| C | Catalyst 531 | g | 2.50 | 2.50 |
| | TOTAL | g | 100 | 100 |

Table 21 shows the mass and % of total mass for the chemical components used to produce a Coating Formulation 17.

TABLE 21

Chemical components used to produce the Coating Formulation 17A.

| COATING FORMULATION 17 | 7409CFT-F15A1P2-1 | | Mass | % |
|---|---|---|---|---|
| A | ATH (FORMULA XIV) | g | 4.00 | 2 |
| B | H2O | g | 225.00 | 90 |
| C | RayCryl 1853 | g | 20.00 | 80 |
| | TOTAL | g | 250.00 | 100 |

Table 22 shows the mass and % of total mass for the chemical components used to produce a Coating Formulation 18.

TABLE 22

Chemical components used to produce the Coating Formulation 17A.

| COATING FORMULATION 17A | 7409WOB-F2PVP1-1 | | Mass | % |
|---|---|---|---|---|
| A | PIP-C4-VINYL (Formula XV) | g | 0.85 | 0.87 |
| B | H2O | g | 79.30 | 81.63 |
| C | TRIBUILD DX-164 (48% solids) | g | 10.00 | 10.29 |
| C | TRICOMEL 100 (41% solids) | g | 7.00 | 7.21 |
| | TOTAL | g | 97 | 100 |

Table 23 shows the mass and % of total mass for the chemical components used to produce a Coating Formulation 18.

TABLE 23

Chemical components used to produce the Coating Formulation 18.

| COATING FORMULATION 18 | 7409WOB-F2VAP05-1 | | Mass | % |
|---|---|---|---|---|
| A | PIP-C4-C2-VINYL-ACETATE (Formula XVII) | g | 0.53 | 0.55 |
| B | H2O | g | 79.30 | 81.90 |
| C | TRIBUILD DX-164 (48% solids) | g | 10.00 | 10.33 |
| C | TRICOMEL 100 (41% solids) | g | 7.00 | 7.23 |
| | TOTAL | g | 97 | 100 |

Table 24 shows the mass and % of total mass for the chemical components used to produce a Coating Formulation 19.

TABLE 24

Chemical components used to produce the Coating Formulation 19.

| COATING FORMULATION 19 | 7409WOB-F14POP1-1 | | Mass | % |
|---|---|---|---|---|
| A | PIP-C6-C2-OH (Formula XVI) | g | 1.44 | 1.44 |
| B | H2O | g | 90.59 | 90.60 |
| C | TRIBUILD DX-164 (48% solids) | g | 5.47 | 5.47 |
| C | TRICOMEL 100 (41% solids) | g | 2.49 | 2.49 |
| | TOTAL | g | 100 | 100 |

Table 25 shows the mass and % of total mass for the chemical components used to produce a Coating Formulation 20.

TABLE 25

Chemical components used to produce the Coating Formulation 20.

| COATING FORMULATION 20 | 7409WOB-F14POP1 | | Mass | % |
|---|---|---|---|---|
| A | PIP-C6-C2-OH (Formula XVI) | g | 1.44 | 1.44 |
| B | H2O | g | 90.59 | 90.59 |
| C | Permafresh 600 | g | 5.48 | 5.48 |
| C | Catalyst 531 | g | 2.49 | 2.49 |
| | TOTAL | g | 100 | 100 |

Table 26 shows the mass and % of total mass for the chemical components used to produce a Coating Formulation 21.

TABLE 26

Chemical components used to produce the Coating Formulation 21.

| COATING FORMULATION 21 | 7409WOB-F14PO3P1 | | Mass | % |
|---|---|---|---|---|
| A | PIP-C3-C2-OH (Formula XVIII) | g | 1.33 | 1.33 |
| B | H2O | g | 90.59 | 90.70 |
| C | Permafresh 600 | g | 5.48 | 5.48 |
| C | Catalyst 531 | g | 2.49 | 2.49 |
| | TOTAL | g | 100 | 100 |

Table 27 shows the mass and % of total mass for the chemical components used to produce a Coating Formulation 22.

TABLE 27

Chemical components used to produce the Coating Formulation 22.

| COATING FORMULATION 22 | 7409WOB-F2V3P2 | | Mass | % |
|---|---|---|---|---|
| A | PIP-C8-C2-VA (Formula XIX) | g | 1.63 | 1.66 |
| B | H2O | g | 79.4 | 81.00 |
| C | Tribuild DX-164 (PVAc) | g | 10.00 | 10.2 |
| C | Tricomel | g | 7.00 | 7.14 |
| | TOTAL | g | 98 | 100 |

Hard-surface coating formulations were prepared that each comprise at least one compound of the general formula II through XXI. These further coating compounds may be suitable for coating hard substrates, such as hard polymers, metals and metal alloys.

Table 28 shows a summary description of the commercially available components used as further components in the following hard-surface coating formulations.

TABLE 28

Description of Further Components in some Hard-Surface Coating Formulations.

| Commercial Products | |
|---|---|
| BECKOPOX ™ EP 2384W/57WA | Type 1 solid epoxy resin as an aqueous dispersion. |

TABLE 28-continued

Description of Further Components in some Hard-Surface Coating Formulations.

| | |
|---|---|
| (BECKOPOX a trademark of Allnex Germany GmbH) | |
| BECKOCURE ® EH 2260/41WA (BECKOCURE is a registered trademark of Allnex Germany GmbH) | Aliphatic polyamine adduct. Suited for anticorrosion coatings. |
| ANCAREZ ™ (ANCAREZ is a trademark used by Air Products and Chemicals, Inc.) AR555 | Solid epoxy dispersion stabilized in water with a nonionic surfactant. |
| ANQUAWHITE ® 100 (ANQUAWHITE is a registered trademark of Air Products and Chemicals, Inc.) | Amine functional polymer dispersed in water and propylene glycol methyl ether |
| Additives | |
| DOWANOL ® PPh (DOWANOL is a registered trademark of the Dow Chemical Company) | Propylene glycol phenyl ether. Slow-evaporating, hydrophobic coalescent. |
| BUTYL CARBYTOL | Diethylene glycol monobutyl ether. Slow-evaporating hydrophilic coalescent. |
| TRICOSIL DMR | Amino functional silicone and emulsifier. Mildly cationic. |
| ADDITOL ® XW 390 (ADDITOL is a registered trademark of the Allnex Germany GmbH) | Flow and wetting agent without silicone. |
| ADDITOL VXW 6374 | Ionic and nonionic surfactant with pigment affinity groups for organic and inorganic pigments. Wetting agent for neutral as well as amine neutralized waterborne coatings systems. |
| DMP ® 30 (DMP is a registered trademark of Air Products and Chemicals, Inc.) | Epoxy cure accelerator (2,4,6 tris(dimethylaminomethyl)phenol) |
| Matrix | |
| E1 | AirProducts ANCAREZ AR555 and ANQUAWHITE 100 |
| E2 | Beckocure EH 2260w/41WA and Beckopox EP 2384w/57WA |
| E9 | Beckocure EH 2260w/41WA |
| F2 | Tribuild DX-164 and Tricomel 100 |

In Table 29 to Table 33, the hard-surface coating formulations that include "*" were separately coated on to Nylon 66 plastic (food grade) and stainless steel 304. The hard-surface coating formulations in Table 34 to Table 40 were coated on to Nylon 66 plastic (NN, food grade). The components of the hard-surface coating formulations in Table 29 to 40 were mixed, coated on to a hard substrate with a hand foam roller and then heated with a heat gun for drying. When dried, the coated hard substrates were cured as indicated in the tables below.

Table 29 shows the mass and % of total mass for the chemical components used to produce a Coating Formulation 23.

TABLE 29

Chemical components used to produce the Coating Formulation 23.

| COATING FORMULATION 23* | E2A1P5-1&2* | Cure: 5 mins at 140° C. | |
|---|---|---|---|
| BECKOPOX EP 2384W/57WA | 75 | 34.42 | 50.04 |
| BECKOCURE EH 2260/41WA (60%) | 100 | 27.37 | 39.79 |
| DI WATER | 12 | 3.74 | 5.44 |
| ATH (40%) (Formula XIV) | | 3.25 | 4.73 |
| Total: | 187 | 68.8 | 100 |

Table 30 shows the mass and % of total mass for the chemical components used to produce a Coating Formulation 24.

TABLE 30

Chemical components used to produce the Coating Formulation 24.

| COATING FORMULATION 24* | E2A1P5-3&4 * | Cure: 5 mins at 140° C. | |
|---|---|---|---|
| BECKOPOX EP 2384W/57WA | 75 | 34.20 | 48.65 |
| BECKOCURE EH 2260/41WA (60%) | 100 | 27.37 | 38.93 |
| DI WATER | 12 | 3.74 | 5.32 |
| DOWANOL PPH | | 1.74 | 2.48 |
| ATH (40%) (Formula XIV) | | 3.25 | 4.62 |
| Total: | 187 | 70.3 | 100 |

Table 32 shows the mass and % of total mass for the chemical components used to produce a Coating Formulation 26.

TABLE 32

Chemical components used to produce the Coating Formulation 26.

Cure: 5 mins at 140° C.

| COATING FORMULATION 26* | E1A1P5-1* | Mass (g) | | |
|---|---|---|---|---|
| | | Theoretical | Practical | % |
| ANCAREZ AR555 | | 75 | 22.23 | 44.47 |
| ANQUAWHITE 100 | | 100 | 10.10 | 20.20 |
| DI WATER | | 12 | 12.50 | 25.01 |
| DOWANOL PPH | | | 1.33 | 2.66 |
| BUTYL CARBYTOL | | | 1.33 | 2.66 |
| ATH (40%) (Formula XIV) | | | 2.50 | 5.00 |
| Total: | | 187 | 50.0 | 100 |

Table 33 shows the mass and % of total mass for the chemical components used to produce a Coating Formulation 27.

TABLE 33

Chemical components used to produce the Coating Formulation 27.

| COATING FORMULATION 27* | E1A1P5-2* | Cure: 5 mins at 140° C. | |
|---|---|---|---|
| ANCAREZ AR555 | 75 | 22.23 | 44.47 |
| ANQUAWHITE 100 | 100 | 10.10 | 20.20 |
| DI WATER | 12 | 10.00 | 20.00 |
| DOWANOL PPH | | 1.33 | 2.66 |
| BUTYL CARBYTOL | | 1.33 | 2.66 |

TABLE 33-continued

Chemical components used to produce the Coating Formulation 27.

| COATING FORMULATION 27* | E1A1P5-2* | Cure: 5 mins at 140° C. | |
|---|---|---|---|
| TRICOSIL DMR | | 2.50 | 5.00 |
| ATH (40%) (Formula XIV) | | 2.50 | 5.00 |
| Total: | | 187 | 50.0 | 100 |

Table 34 shows the mass and % of total mass for the chemical components used to produce a Coating Formulation 28.

TABLE 34

Chemical components used to produce the Coating Formulation 28.

| COATING FORMULATION 28 | NN-E2A1P10-1&2 | Cure: 10 mins at 105-110° C. | |
|---|---|---|---|
| BECKOPOX EP 2384W/57WA | | 75 | 29.46 | 58.92 |
| BECKOCURE EH 2260/41WA (20%) | | 20 | 7.86 | 15.71 |
| ATH (80%) (Formula XIV) | | 12.92 | 5.07 | 10.15 |
| DI WATER | | 19.38 | 7.61 | 15.22 |
| Total: | | 127.3 | 50 | 100.00 |

Table 35 shows the mass and % of total mass for the chemical components used to produce a Coating Formulation 29.

TABLE 35

Chemical components used to produce the Coating Formulation 29.

| COATING FORMULATION 29 | NN-E2A1P10-3&4 | Cure: 10 mins at 150° C. with 6 hour post-cure at 105° C. | |
|---|---|---|---|
| BECKOPOX EP 2384W/57WA | | 75 | 29.16 | 58.32 |
| BECKOPOX EH 2260/41WA (20%) | | 20 | 7.78 | 15.55 |
| ATH (80%) (Formula XIV) | | 12.92 | 5.02 | 10.05 |
| DI WATER | | 19.38 | 7.54 | 15.07 |
| ADDITOL XW 390 | | 1.29 | 0.50 | 1.00 |
| Total: | | 128.59 | 50 | 100.00 |

Table 36 shows the mass and % of total mass for the chemical components used to produce a Coating Formulation 30.

TABLE 36

Chemical components used to produce the Coating Formulation 30.

| COATING FORMULATION 30 | NN-E2A1P6-1&2 | Cure: 10 mins at 150° C. with 6 hour post-cure at 105° C. | |
|---|---|---|---|
| BECKOPOX EP 2384W/57WA | | 75.00 | 25.57 | 51.14 |
| BECKOPOX EH 2260/41WA (50%) | | 50.00 | 17.05 | 34.09 |
| ATH (50%) (Formula XIV) | | 8.08 | 2.75 | 5.51 |
| DI WATER | | 12.12 | 4.13 | 8.26 |
| ADDITOL XW 390 | | 1.46 | 0.50 | 1.00 |
| Total: | | 146.66 | 50 | 100.00 |

Table 37 shows the mass and % of total mass for the chemical components used to produce a Coating Formulation 31.

TABLE 37

Chemical components used to produce the Coating Formulation 31.

| COATING FORMULATION 31 | NN-E2A1P2-1&2 | Cure: 10 mins at 150° C. with 6 hour post-cure at 105° C. | |
|---|---|---|---|
| BECKOPOX EP 2384W/57WA | | 75 | 21.81 | 43.62 |
| BECKOPOX EH 2260/41WA (80%) | | 80 | 23.26 | 46.53 |
| ATH (20%) (Formula XIV) | | 3.23 | 0.94 | 1.88 |
| DI WATER | | 12 | 3.49 | 6.98 |
| ADDITOL XW 390 | | 1.72 | 0.50 | 1.00 |
| Total: | | 171.95 | 50 | 100.00 |

Table 38 shows the mass and % of total mass for the chemical components used to produce a Coating Formulation 32.

TABLE 38

Chemical components used to produce the Coating Formulation 32.

| COATING FORMULATION 32 | NN-E2A1P2-3&4 | Cure: 10 mins at 150° C. with 6 hour post-cure at 105° C. | |
|---|---|---|---|
| BECKOPOX EP 2384W/57WA | | 75 | 19.52 | 39.03 |
| BECKOPOX EH 2260/41WA (100%) | | 100 | 26.02 | 52.04 |
| ATH (20%) (Formula XIV) | | 3.23 | 0.84 | 1.68 |
| DI WATER | | 12 | 3.12 | 6.25 |
| ADDITOL XW 390 | | 1.92 | 0.50 | 1.00 |
| Total: | | 192.15 | 50 | 100.00 |

Table 39 shows the mass and % of total mass for the chemical components used to produce a Coating Formulation 33.

TABLE 39

Chemical components used to produce the Coating Formulation 33.

| COATING FORMULATION 33 | NN-E2A1P2-5&6 | Cure: 10 mins at 150° C. with 6 hour post-cure at 105° C. | |
|---|---|---|---|
| BECKOPOX EP 2384W/57WA | | 75 | 17.66 | 35.32 |
| BECKOPOX EH 2260/41WA (120%) | | 120 | 28.26 | 56.51 |
| ATH (20%) (Formula XIV) | | 3.23 | 0.76 | 1.52 |
| DI WATER | | 12 | 2.83 | 5.65 |
| ADDITOL XW 390 | | 2.12 | 0.50 | 1.00 |
| Total: | | 212.35 | 50 | 100.00 |

Table 40 shows the mass and % of total mass for the chemical components used to produce a Coating Formulation 34.

TABLE 40

Chemical components used to produce the Coating Formulation 34.

| COATING FORMULATION 34 | NN-E2A1P4-1&2 | Cure: 10 mins at 150° C. with 6 hour post-cure at 105° C. | |
|---|---|---|---|
| BECKOPOX EP 2384W/57WA | | 75 | 19.03 | 38.06 |
| BECKOPOX EH 2260/41WA (100%) | | 100 | 25.37 | 50.75 |
| ATH (50%) (Formula XIV) | | 8.08 | 2.05 | 4.10 |
| DI WATER | | 12 | 3.04 | 6.09 |
| ADDITOL XW 390 | | 1.97 | 0.50 | 1.00 |
| Total: | | 197.05 | 50 | 100.00 |

The hard-surface coating formulations in Table 41 to Table 44 were coated on to Nylon 66 Plastic (NN, food grade) and acetal plastic (AL).

Table 41 shows the mass and % of total mass for the chemical components used to produce a Coating Formulation 35. The components of the hard-surface coating formulations in Table 41 through Table 44 were mixed, coated on to a hard substrate with a hand foam roller and then dried at 102° C. and cured for 5 minutes at 140° C.

TABLE 41

Chemical components used to produce the Coating Formulation 35.

| COATING FORMULATION 35 Order of addition | NN/AL-F2D2P1 Product | Supplier | Characteristics | Quantity (g) | Ratio (%) |
|---|---|---|---|---|---|
| A | DEPA (Formula II) | Exigence Technologies | Antimicrobial | 0.16 | 0.9% |
| B | Tribuild DX-164 (PVAc) | Tri-Tex | Binder | 10.00 | 56.5% |
| C | Tricomel | Tri-Tex | Cross-linker | 7.00 | 39.5% |
| D | Dowanol PPH | Dow | Humectant | 0.55 | 3.1% |
|   | TOTAL |   |   | 17.71 | 100.0% |

Table 42 shows the mass and % of total mass for the chemical components used to produce a Coating Formulation 36.

TABLE 42

Chemical components used to produce the Coating Formulation 36.

| COATING FORMULATION 36 Order of addition | NN/AL-F2D2P5 Product | Supplier | Characteristics | Quantity (g) | Ratio (%) |
|---|---|---|---|---|---|
| A | DEPA (Formula II) | Exigence Technologies | Antimicrobial | 2.50 | 5.0% |
| B | H2O | N/A | Solvent | 5.90 | 11.8% |
| C | Tribuild DX-164 (PVAc) | Tri-Tex | Binder | 23.60 | 47.2% |
| D | Tricomel | Tri-Tex | Cross-linker | 16.52 | 33.0% |
| E | Dowanol PPH | Dow | Humectant | 1.49 | 3.0% |
|   | TOTAL |   |   | 50.00 | 100.0% |

Table 43 shows the mass and % of total mass for the chemical components used to produce a Coating Formulation 37.

TABLE 43

Chemical components used to produce the Coating Formulation 37.

| COATING FORMULATION 37 Order of addition | NN/AL-F2D2P10 Product | Supplier | Characteristics | Quantity (g) | Ratio (%) |
|---|---|---|---|---|---|
| A | DEPA (Formula II) | Exigence Technologies | Antimicrobial | 5.01 | 10.0% |
| B | H2O | N/A | Solvent | 11.42 | 22.8% |
| C | Tribuild DX-164 (PVAc) | Tri-Tex | Binder | 19.04 | 38.1% |
| D | Tricomel | Tri-Tex | Cross-linker | 13.33 | 26.7% |
| E | Dowanol PPH | Dow | Humectant | 1.20 | 2.4% |
|   | TOTAL |   |   | 50.00 | 100.0% |

Table 44 shows the mass and % of total mass for the chemical components used to produce a Coating Formulation 38.

TABLE 44

Chemical components used to produce the Coating Formulation 38.

| COATING FORMULATION 38 Order of addition | NN/AL-F2D2P15 Product | Supplier | Characteristics | Quantity (g) | Ratio (%) |
|---|---|---|---|---|---|
| A | DEPA (Formula II) | Exigence Technologies | Antimicrobial | 7.49 | 15.0% |
| B | H2O | N/A | Solvent | 17.50 | 35.0% |
| C | Tribuild DX-164 (PVAc) | Tri-Tex | Binder | 14.00 | 28.0% |
| D | Tricomel | Tri-Tex | Cross-linker | 9.80 | 19.6% |
| E | Dowanol PPH | Dow | Humectant | 1.20 | 2.4% |
| | TOTAL | | | 50.00 | 100.0% |

The hard-surface coating formulations in Table 45 were coated on to a galvanized-steel substrate.

Table 45 shows the mass and % of total mass for the chemical components used to produce a Coating Formulation 39. The components of Coating Formulation 39 were mixed, applied to a galvanized steel substrate with a hand-foam roller and dried with a heat gun. Multiple coats of the Coating Formulation 39 may have been applied after drying and before curing. The Coating Formulation 39 was cured at 90° C. for 3 hours followed by a post-cure of 130° C. for 30 minutes.

TABLE 45

Chemical components used to produce the Coating Formulation 39.

| COATING FORMULATION 39  GS-E9PDP15 | | | Before Curing |
|---|---|---|---|
| BECKOPOCK EP 2384/57WA | 100.00 | 36.17 | 72.33% |
| PIP-C4-BIS-C3-NH2 (50%) (Formula XX) | 18.18 | 6.58 | 13.15% |
| Water | 18.00 | 6.51 | 13.02% |
| BMP 30 (epoxy/amine cure accelerator - 2,4,6 Tris (dimethylaminomethyl) phenol | 2.07 | 0.75 | 1.50% |
| Total: | 138.25 | 50.00 | 100.00% |

Table 46 shows the mass and % of total mass for the chemical components used to produce a Coating Formulation 40.

TABLE 46

Chemical components used to produce the Coating Formulation 40.

| Coating Formulation 40 GS-E9PDP15-5&6 | Mass (g) Theoretical | Mass (g) Practical | Percentage Before Curing | Percentage After curing | Notes |
|---|---|---|---|---|---|
| BECKOPOCK EP 2384/57W | 100.00 | 21.70 | 72.33% | 84.61% | Curing at 90° C. for 3 hours and post cure at 130° C. for 0.5 hr |
| PIP-C4-BIS-C3-NH2 (Formula XX) | 18.18 | 3.95 | 13.15% | 15.39% | |
| Water | 18.00 | 3.91 | 13.02% | | |
| DMP 30 (epoxy/amine cure accelerator - 2,4,6 Tris (dimethylaminomethyl) phenol | 2.07 | 0.45 | 1.50% | | |
| Total: | 138.25 | 30.00 | 100.00% | 100.00% | |

Table 47 shows the mass and % of total mass for the chemical components used to produce a Coating Formulation 41.

TABLE 47

Chemical components used to produce the Coating Formulation 41.

| Coating Formulation 41 | Mass (g) | | Percentage Before | Percentage After | |
|---|---|---|---|---|---|
| GS-E9PDP15-9&10 | Theoretical | Practical | Curing | curing | Notes |
| BECKOPOCK EP 2384/57W | 100.00 | 21.70 | 72.33% | 84.61% | Curing at 90 ° C. for 3 hours and post cure at 130° C. for 0.5 hr Processing: Apply 2-3 times after drying with heat gun |
| PIP-C4-BIS-C3-NH2 (Formula XX) | 18.18 | 3.95 | 13.15% | 15.39% | |
| Water | 18.00 | 3.91 | 13.02% | | |
| DMP 30 (epoxy/amine cure accelerator - 2,4,6 Tris (dimethyl-aminomethyl) phenol | 2.07 | 0.45 | 1.50% | | |
| Total: | 138.25 | 30.00 | 100.00% | 100.00% | |

Table 48 shows the mass and % of total mass for the chemical components used to produce a Coating Formulation 42.

TABLE 48

Chemical components used to produce the Coating Formulation 42.

| Coating Formulation 42 | Mass (g) | | Percentage Before | Percentage After | |
|---|---|---|---|---|---|
| GS-E9PDP15-11&12 | Theoretical | Practical | Curing | curing | Notes |
| BECKOPOCK EP 2384/57W | 100.00 | 21.70 | 72.33% | 84.61% | Curing at 90° C. for 3 hours and post cure at 130° C. for 0.5 hr Processing: Apply 2-3 times after drying with heat gun |
| PIP-C4-BIS-C3-NH2 (Formula XX) | 18.18 | 3.95 | 13.15% | 15.39% | |
| Water | 18.00 | 3.91 | 13.02% | | |
| DMP 30 (epoxy/amine cure accelerator - 2,4,6 Tris (dimethyl-aminomethyl) phenol | 2.07 | 0.45 | 1.50% | | |
| Total: | 138.25 | 30.00 | 100.00% | 100.00% | |

Chlorination Measurements

Coated substrate samples were tested for chlorine loading propensity, chlorine loading kinetics, and for antibacterial efficacy. The effect of accelerated life cycles on durability was also investigated. This section describes the measurements of chlorination.

As comparative samples for the coated textile substrates, two commercially available sportswear textiles: LULU-LEMON, SILVERSCENT product that incorporates the X-STATIC silver product and an UNDER ARMOUR product with Scent Control technology that comprises a blend of at least silver and zinc were tested. As a further comparative sample, a commercially available CLOROX® (CLOROX is a registered trademark of The Clorox Company) product that is a textile coated with N-chloramine (Clorox) was examined. Collectively, these commercially available, modified textiles and the substrate samples that are coated with the coating formulations, as described above, may be referred to herein as the Coated Samples.

All of the Coated Samples that were tested for mass changes were cut to 1"×1" squares. For the comparative analysis samples branded as LuluLemon, Under Armour and Clorox were treated the same way. However, due to differences in the sample properties (weave and the density) and the yarn properties (fiber material, fiber density, yarn construction) the mass and specific surface area of the samples may not be the same, in spite of having a substantially similar 2D size. The average weights of these 1×1 inch samples can be seen in Table 14 below.

TABLE 49

Average mass of the coated samples.

| Sample Type | Average Mass of 1" × 1" Sample |
|---|---|
| AS1 | 0.0720 g |
| NC2 | 0.0728 g |
| LuluLemon | 0.1067 g |
| Under Armour | 0.1010 g |
| Clorox | 0.1664 g |

To chlorinate the Coated Samples, 50 mL of ultrapure water was added to a 250 mL Erlenmeyer flask. A bleach solution of 72678 ppm of chlorine was then added to the flask to achieve the desired chlorination solution concentration (68.79 µL to achieve 100 ppm, and 1031 µL to achieve 1500 ppm). After briefly stirring the bleach into the solution, the uncoated samples were added and secured in a shaker, and then shaken for 1 hour. After an hour, the solution was drained from the flask and washed 4 times with distilled water to remove excess chlorine. The Coated Samples were then set out for an hour in open air to dry.

The concentration of active chlorine on the fabric samples was analyzed by a traditional iodometric titration method. Each 1×1 inch sample was immersed in a solution of 30 mL distilled water and 25 mL of 0.001N sodium thiosulfate standard solution. After stirring in a 100 mL beaker with a magnetic stir rod for 60 min, 2 mL of 5% acetic acid buffer solution was added. Then, with continued stirring, the solution was titrated with 0.001N iodine standard solution by monitoring millivolt changes with a redox electrode (platinum Ag/AgCl). The active chlorine concentration of the samples was then calculated from the following general formula (XX):

$$[Cl^+](ppm) = \frac{35.45 \times (V_1 - V_2) \times N \times 1000}{(2 \times W)}. \quad [XX]$$

where V1 and V2 are the volumes (mL) of the iodine solution consumed in titrations of blank sodium thiosulfate solution and that with PET sample in, respectively. N is the normality of iodine solution; and W is the weight of the samples in grams. This process was done for each final product to determine the active chlorine concentrations resulting from chlorination for both AS1 and NC2 samples.

Figure 7:
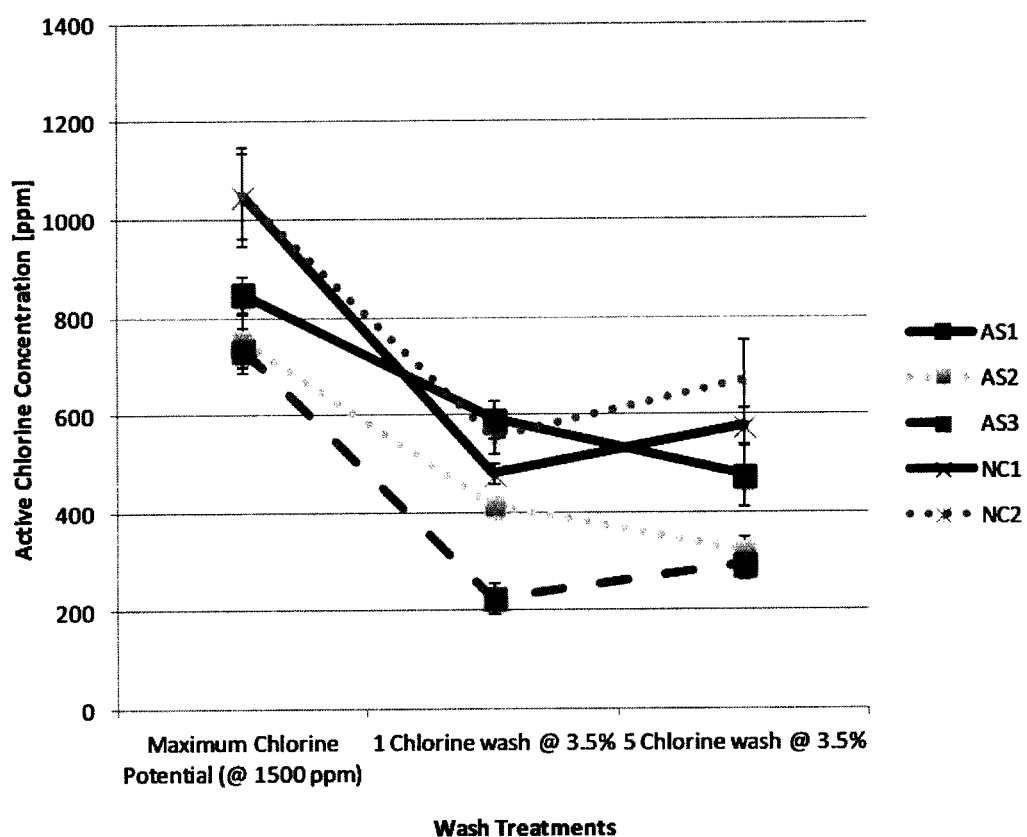
FIG. 7 is a line graph that depicts representative chlorination data obtained from substrates coated in coating formulations of the present disclosure after a number of chlorine washes.

Quantitative measurements of the chlorine loading on each substrate sample provide context for the antibacterial test results provided below. FIG. 7 depicts the active chlorine concentration (ppm) compared with the various chlorination level of samples coated with the Coating Formulations 1, 2 and 3 and samples coated with the Coating Formulations 4 and 5.

As indicated by the second and third data points for each sample in FIG. 7, the second and third data points are different from the first data point, labelled maximum chlorine potential at 1500 ppm. The wash cycles were conducted according to AATCC 188-2010, "Colorfastness to Sodium Hypochlorite Bleach in Home Laundering." The second and third data points may provide useful insight into the durability of the various coatings as well as a comparison to the theoretical maximum chlorine loading potential of each sample.

The samples that were coated with the AS1 and NC2 formulations were selected for further testing. 1500 ppm of chlorine is an unrealistically high level of chlorine in the recharge solution for most recharging environments. Accordingly, 100 ppm was selected as an appropriate concentration for the recharge solution as this amount represents a level that is at or below generally accepted no-rinse level of chlorine wash for surfaces in food-manufacturing environments or food-processing environments.

Figure 8:
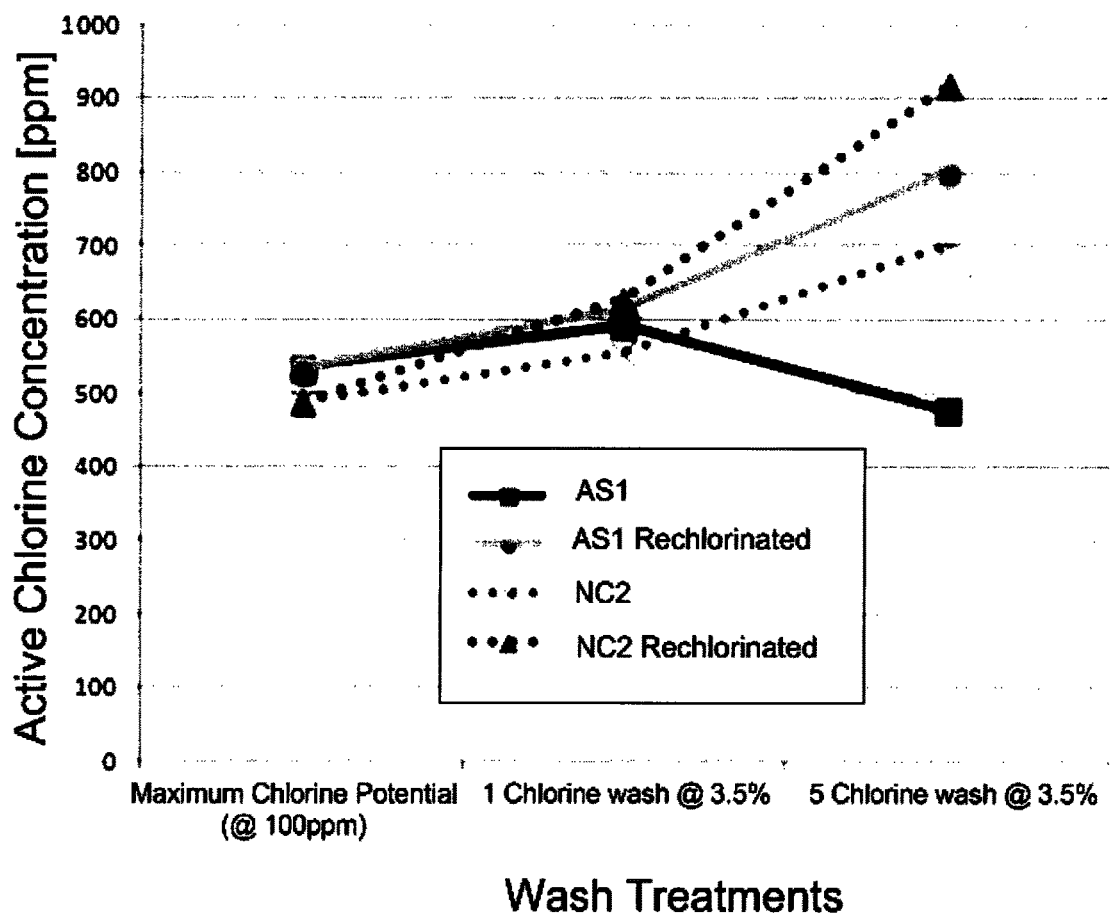
FIG. 8 is a line graph that depicts representative re-chlorination data obtained from substrates coated with coating formulations of the present disclosure after a number of chlorine washes.

Non-chlorinated substrate samples that were coated with AS1 and NC2 were chlorinated per the previously discussed procedure at a concentration of 100 ppm. The samples, washed per AATCC 188-2010, were also re-chlorinated per the same procedure to evaluate their propensity to achieve a higher chlorine loading following the chlorine wash cycle, still using 100 ppm chlorine in the wash cycle. FIG. 8 depicts the representative date obtained from these tests.

For comparison, commercially available N-chloramine towels (Chlorox®) were also chlorinated at 100 ppm. Using the same chlorination and titration procedures, active chlorine loading was determined to be 72 ppm on these commercially available towels, which were used in the biocidal activity assessment, as described herein below.

The chlorination uptake was also measured in the following examples of Coating Formulations 10 through 48.

Table 50 shows an example of idiometric titration data that reflects active-chlorine uptake of Coating Formulations 10 to 16 when coated on polycotton and following exposure to 100 ppm chlorine for one hour of shaking.

TABLE 50

Summary of chlorine uptake data for Coating Formulations 10 to 16.

Summary of Results

| Coating Formulation | SAMPLE ID | Active Chlorine (PPM) |
|---|---|---|
| 10 | 7409CFT-F2D2P1-1 | 247 |
| 11 | 7409CFT-F2D2P1-3 | 388 |
| 12 | 7409CFT-F11D2P1-1 | 274 |
| 13 | 7409CFT-F12A1P2-1 | 64 |
| 14 | 7409CFT-F13A1P2-1 | 46 |
| 15 | 7409CFT-F14D2P1-1 | 309 |
| 16 | 7409CFT-F14H1P1-1 | 259 |
| 16 | 7409CFT-F14H1P1-2 | 248 |

Table 51 shows an example of idiometric titration data that reflects active-chlorine uptake of Coating Formulations 17A, 18 and 19 when coated on polycotton and following exposure to 100 ppm chlorine for 5 minutes of shaking.

TABLE 51

Summary of chlorine uptake data for Coating Formulations 17A, 18 and 19.

| Coating Formulation | SAMPLE ID | Active Chlorine (PPM) | Standard Deviation |
|---|---|---|---|
| 17A | 7409WOB-F2PVP1-1 | 84 | 5 |
| 18 | 7409WOB-F2VAP05-1 | 266 | 9 |
| 19 | 7409WOB-F14POP1-1 | 36 | 21 |

Table 52 shows an example of idiometric titration data that reflects active-chlorine uptake of Coating Formulations 17A, 18 and 19 when coated on polycotton and following exposure to 100 ppm chlorine for 60 minutes of shaking.

TABLE 52

Summary of chlorine uptake data for Coating Formulations 17A, 18 and 19.

| Coating Formulation | SAMPLE ID | Active Chlorine (PPM) | Standard Deviation |
|---|---|---|---|
| 17A | 7409WOB-F2PVP1-1 | 206 | 18 |
| 18 | 7409WOB-F2VAP05-1 | 451 | 17 |
| 19 | 7409WOB-F14POP1-1 | 30 | 15 |

Table 53 shows an example of idiometric titration data that reflects active-chlorine uptake of Coating Formulations 20, 21 and 22 when coated on polycotton and following exposure to 100 ppm chlorine for 60 minutes of shaking.

TABLE 53

Summary of chlorine uptake data for Coating Formulations 20, 21 and 22.

| Coating Formulation | SAMPLE ID | Active Chlorine (PPM) | Standard Deviation |
|---|---|---|---|
| 20 | 7409WOB-F14POP1-5 | 82 | 14 |
| 21 | 7409WOB-F14PO3P1-1 | 95 | 13 |
| 22 | 7409WOB-F2V3P2-1 | 142 | 15 |

Table 54 shows an example of idiometric titration data that reflects active-chlorine uptake of a virgin sample of polycotton that was exposed to 100 ppm for 60 minutes with wrist action shaking.

TABLE 54

Summary of virgin polycotton chlorine loading.

| Sample Set | Sample ID | Shaking Type | Weight (g) | Control Value I2 (ml) | Consumed Iodine I2 (ml) | Active Chlorine (ppm) |
|---|---|---|---|---|---|---|
| 7409CFT_virgin | 1A | wrist action | 0.252 | 25.5 | 25.4 | 7.0343254 |
|  | 1B | wrist action | 0.2484 | 25.5 | 25.4 | 7.1362721 |
|  | 1C | wrist action | 0.2491 | 25.5 | 25.5 | 0 |
|  |  |  |  |  | Average | 4.7235325 |
|  |  |  |  |  | Standard Deviation | 4.0910167 |

The active-chlorine loading of the hard surfaces that were coated with Coating Formulations 24 to 48 was tested. The steel substrate surfaces were not tested for active-chlorine uptake. Briefly, after exposing the coated substrate to chlorine the substrate was washed 4-5 times in distilled water, pat down with a towel and then allowed to air dry. The following modification of the iodiometric-titration method described above was performed:

For each sample, a solution of 25 mL 0.001N sodium thiosulfate and 30 mL of ultrapure water was prepared in a 100 mL beaker. A magnetic stirring bar and one sample was added to each of the filled beakers. Each sample was stirred for a full hour before testing. The burette was rinsed with iodine solution three times before use. The burette was then filled with iodine solution and set up in a holder over the stirring base. While the samples were in the stirring process the titration control was performed. A volumetric pipette was used to add the same volume of sodium thiosulfate solution as to what was used for the quenching of samples in a 100 mL beaker with 30 mL ultrapure water. A small stirring bar was added to the beaker as was 2 mL a 5% acetic acid buffer and then stirring was commenced.

The electrode was set up erectly in the beaker and the start button on the conductivity/pH benchtop meter was pressed to electric potential mode (mV). Iodine solution was added while observing the mV change shown on the pH meter. Electric potential (mV) first decreased then increased with the addition of the iodine solution. The endpoint of this titration is the point at which the electric potential shows a sudden jump. As for this titration the electric potential change is significant, so the mV change was used as the signal of endpoint. Record the ending reading in the burette. ΔV in this process is just the V1 in equation (2).

After stirring for an hour 2 mL of the acetic acid buffer was added to the beaker of each sample, again the volume reading on the burette was noted.

From this point, each sample was titrated where ΔV in this process is the V2 in the equation A (Eq. A) which can be used to calculate the active chlorine concentration on the hard surface as follows:

$$\text{Active Chlorine } [Cl^+]\left(\frac{\mu g}{cm^2}\right) = \frac{35.45\left(\frac{g}{mol}\right) \times (V_1 - V_2)(mL)}{\left(\frac{L}{1000\ mL}\right) \times N\left(\frac{mol}{L}\right) \times 1000000}{2 \times A(cm^2)} \quad \text{(Eq. A)}$$

where V1 and V2 are the volumes (mL) of the iodine solution consumed in titrations of the sodium thiosulfate control and the chlorinated sample respectively. N is the normality of iodine solution (eq. mol/L) and A is the surface area of the sample in cm$^2$.

Table 55 shows an example of idiometric-titration data that reflects active-chlorine uptake of Coating Formulations 24, 26, 27, 28, 30, 31, 32 and 33 when coated on a hard, non-porous surface and following exposure to 100 ppm chlorine for 60 minutes of shaking.

TABLE 55

Summary of chlorine uptake data for Coating Formulations 24, 26, 27, 28, 30, 31, 32 and 33.

| Coating Formulation | Sample | Active Chlorine (μg/cm$^2$) | STD |
|---|---|---|---|
| 24 | E2A1P5-3 | 0.1932 | 0.2652 |
| 26 | E1A1P5-1 | 0.7988 | 0.4043 |
| 27 | E1A1P5-2 | 0.6264 | 0.3963 |
| 28 | NN-E2A1P10-1 | 3.4266 | 1.0435 |
| 30 | NN-E2A1P6-1 | 0.8243 | 0.1028 |
| 31 | NN-E2A1P4-3 | 0.1607 | 0.2932 |
| 31 | NN-E2A1P2-2 | 0.1788 | 0.0697 |
| 33 | NN-E2A1P2-6 | 0.1513 | 0.1340 |
| 32 | NN-E2A1P2-4 | 0.4597 | 0.0135 |

Table 56 shows an example of idiometric-titration data that reflects active-chlorine uptake of Coating Formulations 35, 36, 37 and 38 when coated on a hard, non-porous surface and following exposure to 100 ppm chlorine for 60 minutes of shaking or an overnight soak in 100 ppm chlorine.

TABLE 56

Summary of chlorine uptake data for Coating Formulations 35, 36, 37 and 38.

| Coating Formulation | SAMPLE ID | Active Chlorine (ug/cm2) | Std Deviation |
|---|---|---|---|
| 35 | NN-F2D2P1-(nylon) | 3.32 | 0.77 |
| 35 | AL-F2D2P1-(acetal) | 5.46 | 0.88 |
| 36 (overnight) | NN-F2D2P5- | 2.67 | 0.48 |
| 37 (overnight) | NN-F2D2P10- | 1.41 | 0.68 |
| 38 (overnight) | NN-F2D2P15- | 1.99 | 0.43 |

Table 57 shows an example of idiometric-titration data that reflects active-chlorine uptake of Coating Formulations 35, 37 and 38 when coated on to a hard, non-porous surface and following exposure to 200 ppm chlorine for 30 minutes of shaking.

TABLE 57

Summary of chlorine uptake data for Coating Formulations 35, 36, 37 and 38.

Summary of Results

| Coating Formulation | SAMPLE ID | Active Chlorine (ug/cm2) | Std Deviation |
|---|---|---|---|
| 35 | NN-F2D2P1- | 3.49 | 1.04 |
| 37 | NN-F2D2P10- | 4.69 | 0.22 |
| 38 | NN-F2D2P15- | 4.11 | 0.52 |

Table 58 provides an example of idiometric-titration data that reflects active-chlorine uptake of Coating Formulation 40 and 41 when coated on a hard, non-porous surface and following exposure to 100 ppm chlorine for 10 minutes (Coating Formulation 41) or 60 minutes (Coating Formulation 40) of shaking.

TABLE 58

Summary of chlorine uptake data for Coating Formulation 40 and 41.

| Coating Formulation | Sample 100 ppm 10 or 60 minutes | Active Chlorine | STD |
|---|---|---|---|
| 41 | E9PDP15-9 (10 minute) | 6.11 | 0.23 |
| 40 | E9PDP15-5 (60 minute) | 5.9961 | 1.0189 |

Durability Testing

To test durability, several of the Coated Samples were subjected to the AATCC Test Method 61 (Test 2A Procedure). For the durability testing, 15×4 inch samples were laundered in a laundrometer each in a canister containing 50 small steel ball bearings and a solution of 0.225 g detergent (without OBO from Test Fabrics inc.) and 150 mL ultra-pure water.

Water temperatures in the washing apparatus were set to about 49° C. and each sample was put through different lengths of wash cycles. Due to the mechanical abrasion initiated by the steal ball bearings, each of the 45 minute cycles in the laundrometer is equated to five normal home laundering cycles. Each sample was put through the equivalent of either 5, 25, 50 and 100 cycles. Samples were then taken out of their canisters and rinsed three times with distilled water to remove any excess detergent. The samples were then allowed to dry, and were chlorinated using the procedure discussed above, at 100 ppm, followed by a quantitative measurement of the active chlorine on the fabric surface.

Figure 9:
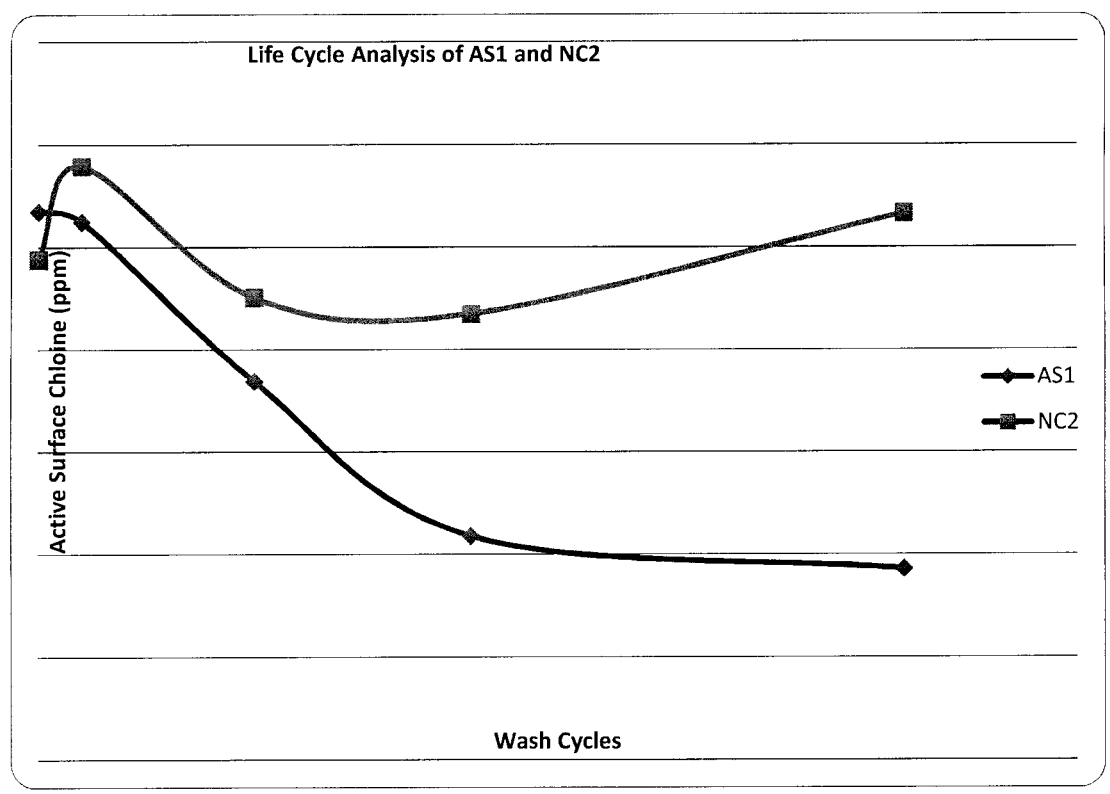
FIG. 9 is a line graph that depicts representative active surface chlorine levels data obtained from substrates coated in coating formulations of the present disclosure after different numbers of wash cycles.

To evaluate the durability of the coating formulations, both NC2 and AS1 were tested according to AATCC Test Method 61 (Test 2A Procedure). FIG. 9 depicts the chlorination levels versus a number of wash cycles for the substrate sample that is coated with the AS1 and the substrate sample that is coated with the NC2 formulation. The NC1 coated substrate demonstrated a relatively stable chlorination propensity over the simulated life cycles. The AS1 samples demonstrated a degrading performance over more wash cycles. Chlorination was done after the wash cycles at 100 ppm, and neither of the samples was chlorinated prior to the wash cycles. This result is in line with expectations regarding the greater durability of the Coating Formulations 4 through 9 as compared with the Coating Formulations 1, 2 or 3.

Table 59 summarizes the active-chlorine content of a coated substrate that has been coated with Coating Formulation 10, 11, 12, 15 and 16 and then run through 0 or 50 cycles within laudrometer, as described above, followed by exposure to 100 ppm of chlorine for 60 minutes.

TABLE 59

A Summary of Durability Analysis of Coating Formulations 10, 11, 12, 15 and 16.

| Coating Formulation | SAMPLE ID | Cycle Count | Active Chlorine (PPM) | Standard Deviation |
|---|---|---|---|---|
| 10 | 7409CFT-F2D2P1-1 | 0 cycles 50 cycles | 247 | 16.5 |
| 11 | 7409CFT-F2D2P1-3 | 0 cycles 50 cycles | 388 262 | 4.0 23.8 |
| 12 | 7409CFT-F11D2P1-1 | 0 cycles 50 cycles | 274 302 | 30.4 13.9 |
| 15 | 7409CFT-F14D2P1-1 | 0 cycles 50 cycles | 309 144 | 21.7 5.6 |
| 16 | 7409CFT-F14H1P1-2 | 0 cycles 50 cycles | 248 305 | 4.0 27.9 |

Table 60 summarizes the active-chlorine content of a coated substrate that has been coated with Coating Formulation 17A, 18, and 19 then run through 50 cycles within laudrometer, as described above, followed by exposure to 100 ppm of chlorine for 60 minutes.

TABLE 59

A Summary of Durability Analysis of Coating Formulations 17A, 18, and 19.

| Coating Formulation | SAMPLE ID | Active Chlorine (PPM) | Standard Deviation |
|---|---|---|---|
| 17A | 7409WOB-F2PVP1-1 | 306 | 22 |
| 18 | 7409WOB-F2VAP05-1 | 313 | 11 |
| 19 | 7409WOB-F14POP1-1 | 127 | 17 |

To investigate the cure state of the polymer system within some of the hard-surface coating formulations, a series of differential scanning calorimetry (DSC) analysis were done using parameters from ASTM E1356-08 section 10 on a TA Instruments DSC Q2000. Briefly, the following DSC analysis were completed for PD compound:

1. Isothermal in which uncured Coating Formulation is subjected to a temperature hold for a specific amount of time. The data indicated reaction completion.
2. Tg shift in which cured material is twice cycled through a ramp rate. The first provides a value for what the temperature of a glass-like state (Tg) the first cycle achieved. The second run indicates the ultimate Tg that could be achieved.
3. Dynamic in which uncured material is subjected to a temperature ramp rate, which provides an optimal curing temperature between DGEBA and PD compound is.

A Tg shift analysis was performed only for the ATH(A1) compound because a highly cured structure was not obtainable with the mono-amine functionality. It is well known that there is a near 1:1 relationship between degree of cure and Tg in epoxy amine systems. This relationship is not always perfect due to variability in mass, mixing and the like. Table 60 summarizes examples of the DSC analysis.

were 1, 2, 4 and 6 hours. Then, the samples were quenched with 5.0 mL of sterile 0.05M sodium thiosulfate solution to

TABLE 60

Summary of DSC analysis of Coating Formulation 30 (E2A1P6), 32 (E2A1P2) and Coating Formulation 40 (E9PDP15-5).

| Compound | Test Type | DSC ID | Ramp Rate | Max Temp | Min Temp | Tg Actual |
|---|---|---|---|---|---|---|
| Control | Tg Shift | E2NA_P0-2 | 10° C./min | 230° C. | 20° C. | 42.94° C. |
| A1 | Tg Shift | E2A1_P2-1 | 10° C./min | 230° C. | 0° C. | 41.58° C. |
| A1 | Tg Shift | E2A1_P6-1 | 10° C./min | 230° C. | 20° C. | N/A |
| PD | Isothermal | PIP-C4-C3-100-2 | none | 65° C. | 65° C. | N/A |
| PD | Tg Shift | E8PD_P35-1 | 10° C./min | 200° C. | 20° C. | 67.67 |
| PD | Dynamic Run | E8PDP35_DMSO-1 | 10° C./min | 175° C. | 20° C. | N/A |
| PD | Tg Shift | E9PDP15-B-1 | 10° C./min | 200° C. | 20° C. | 71.17° C. |
| PD | Tg Shift | E9PDP15-C-1 | 10° C./min | 200° C. | 20° C. | 66.88° C. |
| PD | Tg Shift | E9PDP15-5 | 10° C./min | 190° C. | 20° C. | 73.99° C. |

| Compound | Tg | Comments |
|---|---|---|
| Control | 50.03° C. | Beckopox EP 2384 and Beckocure EH 2260. Commercial mix |
| A1 | 53.85° C. | Profile of Tg shift indicated residual curing occurring. The curing indicates further reaction occurring. Tg values similar to commercial control. 80% Beckopox + 20% ATH |
| A1 | N/A | Cure was not to sufficient completion. Data produced indicated the formulation was poorly cured. 50% Beckopox + 50% ATH |
| PD | N/A | Isothermal hold at 65 C. for two hours. The PD compound was dissolved into methanol and blended with DGEBA at 100% stoichiometric content. Data indicates reaction comes to completion after 2 hr soak in DSC scale. |
| PD | 107.19° C. | E8PDP35-1, PD and DGEBA at 1:1 Stoichiometric ratio. Cured at 100° C. for .5 hours. |
| PD | 107.36° C. | Dynamic run with E8PDP35 in DMSO. Temperature limited so that solvent does not evaporate. Second run ultimate TG indicated at 107.36° C. Data corresponds to TG shift analysis. Data indicates curing exothermic reaction terminates at 103° C. Optimal cure cycle is then ~100° C. for PD and DGEBA. |
| PD | 86.15° C. | Tg shift with Beckopox resin system at 1:1 Stoichiometric ratio. Sample was cured at 90° C. for 2 hours. Addition of DMP 30 accelerator for improved TG. Data compared to E9PDP15-C-1 indicates improved Tg. |
| PD | 87° C. | Tg shift with Beckopox resin system at 1:1 Stoichiometric ratio. Sample was cured at 90° C. for 2 hours. No DMP added. |
| PD | 82.65° C. | Tg shift with Beckopox resin system at 1:1 Stoichiometric ratio. Sample was cured at 90° C. for 3 hours with DMP accelerator. This was done as a secondary check to ensure data is consistent. Sample was then used in testing. |

In general the DSC data indicates that the polymer system of Coating Formulation 30 (E2A1P6), 32 (E2A1P2) and Coating Formulation 40 (E9PDP15-5) formed adequately cured polymer systems. For Coating Formulation 40 (E9PDP15-5) the data indicates reactivity is feasible at various time and temperature conditions.

Biocidal Activity Assessment

The biocidal properties of various of the Coated Samples were examined against clinical isolates of CA-Methicillin-resistant Staphylococcus aureus (MRSA) (#40065, community-associated) and E. coli (ATCC 25922) using a "sandwich test" modified from AATCC 100 standard testing method. Logarithmic-phase bacterial cultures were prepared by initially suspending several colonies in tap/hard water at a density equivalent to 0.5 McFarland standard of $10^8$ colony-forming units (CFU)/mL, and then diluted 100 times to $10^6$ CFU/mL. 20 µL of the diluted CA-MRSA and E. coli (ATCC 25922) solutions were added into 60 mL of Tryptone Soya Broth and MacConkey Broth, respectively. After 16-18 hour incubation at 37° C., the logarithmic-phase bacterial cultures were ready for use. The test fabrics were cut into square swatches (1×1 inch), one of which was put in a sterilized container. 100 µL of the logarithmic-phase bacterial suspensions ($5\times10^5$-$1\times10^6$ CFU/mL) was added to the swatch center and then sandwiched with another piece of swatch. The whole "sandwich" set was held in place by sterile weights. The contact times for chlorinated samples were 1, 5, 10, 30 and 60 min, while for silver coated samples were 1, 2, 4 and 6 hours. Then, the samples were quenched with 5.0 mL of sterile 0.05M sodium thiosulfate solution to remove all oxidative chlorine, followed by 2 min of vortexing and 1 min of sonication. Serial dilutions of the solutions of vortexed and sonicated bacteria were made in tap/hard water, and they were plated on Tryptone Soya Agar. The plates were incubated at 37° C. for 24 h, and viable bacterial colonies were recorded for bactericidal efficacy analysis. The percentage reduction of bacteria (%)=(A−B)/A×100; and the logarithm reduction=log (A/B) if B>0; =log (A) if B=0, where A is the number of bacteria from blank control, and B is the number of bacteria recovered from the inoculated test specimen swatches.

Commercially available N-chloramine treated fabric (Clorox) was also selected for assessing the biocidal activity. Due to its high absorbency and fluffy texture, it is difficult to fully extract bacterial cells from the Clorox sample in merely 5 mL of neutralizer (sodium thiosulfate) solution. Instead, the original AATCC 100 test method was used, where 1 mL of bacterial suspension ($5\times10^5$-$1\times10^6$ CFU/mL) were completely absorbed by 2 pieces of square swatches 1×1 inch of N-chloramine treated fabrics (Clorox). At a selected time point, bacterial cells were extracted in 100 mL of sterile 0.05M sodium thiosulfate solution, following 2 min of vortexing and 1 min of sonication. Serial dilutions were made and plated on Tryptone Soya Agar, and viable colonies were recorded after 24-hour incubation at 37° C.

MRSA is one of the most frequently isolated organisms that contributes to healthcare associated infections (HAIs). Thus, it was selected to evaluate the biocidal activity of the coated substrates 12A along with the other commercially available modified textile products described above.

Figure 10:
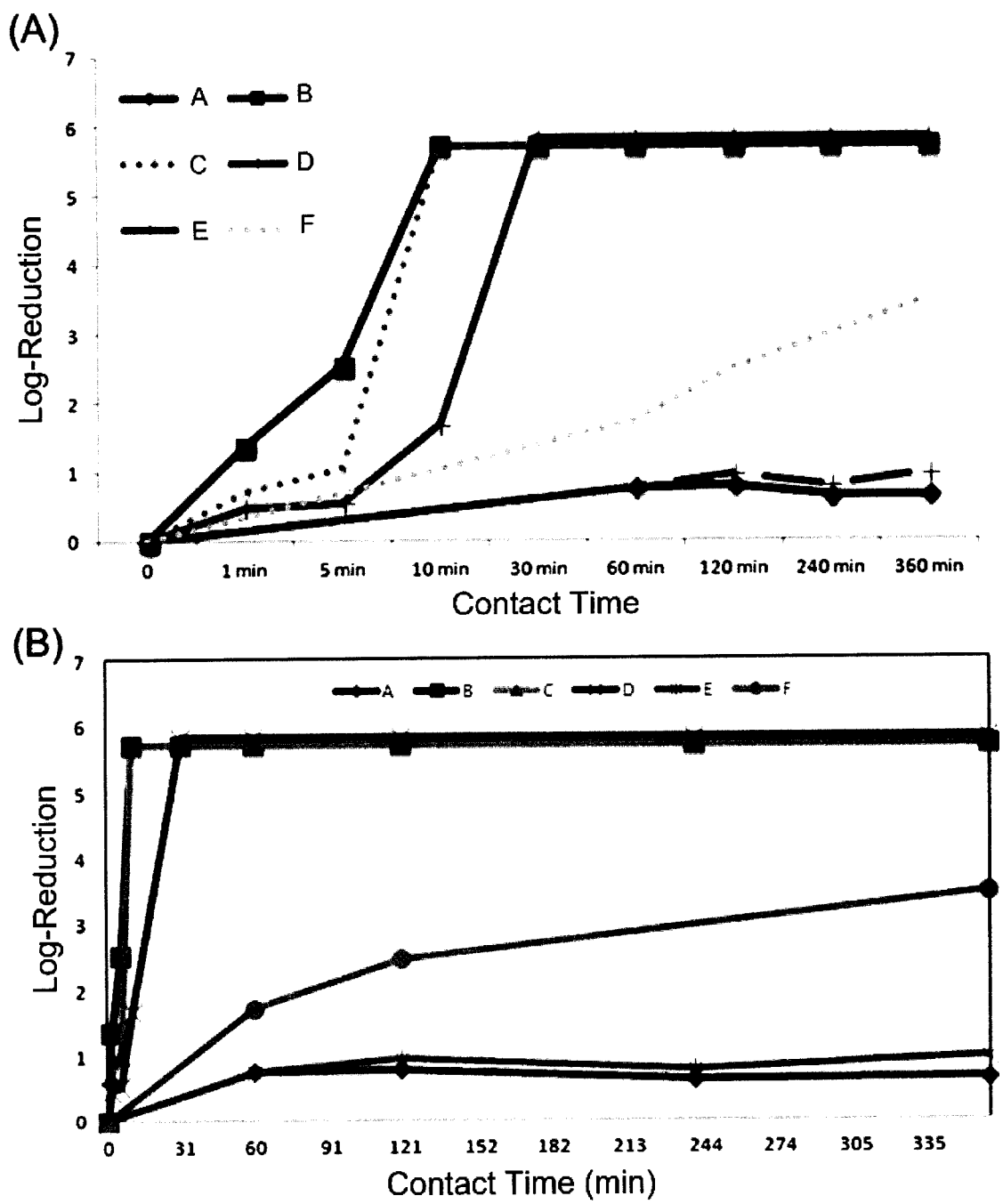
FIG. 10A and FIG. 10B are both line graphs that depict representative biocidal activity data obtained from substrates coated in coating formulations of the present disclosure and other modified textiles that were exposed to Methicillin-resistant *Staphylococcus aureus* (MRSA)

FIG. 10A and FIG. 10B depict the bacterial reduction (log) as a function of contact time between MRSA and the Coated Samples. FIG. 10A and FIG. 10B represent the same data with different contact times (x-axis) provided. In FIG. 10A and FIG. 10B, line A represents Pristine Substrate; line B represents the AS1 coated substrate sample; line C represents the NC2 coated substrate sample; line D represents the Clorox sample; line E represents the Under Armour sample; and line F represents the Lululemon sample.

FIG. 10A and FIG. 10B show that both AS1 and NC2 demonstrated a superior biocidal activity, arriving at a total killing of 5.70-log reduction of MRSA within 10 min. The AS1-coated substrate had the fastest killing kinetics with 2.52-log reduction at 5 min. Quantitative chlorine loading measurements on identical fabric samples, chlorinated using the same procedure, indicated 535 ppm chlorine. A 1.03-log reduction was achieved by the NC2-coated fabric in 5 minutes.

The Clorox sample exhibited less efficient biocidal activity than both of the AS1 and NC2 samples, reaching a 1.67-log reduction at 10 min and killing substantially all the bacteria at 30 min. Although the concentration of active chlorine of the commercial N-chloramine treated fabric (Clorox) was 72 ppm, much lower than that of AS1 or NC2 coated samples, the antibacterial activity was still comparable. Without being bound by any particular theory, it is expected the enhanced efficacy of the quaternized N-chloramines (i.e. AS1 and NC1) over regular N-chloramines (Clorox). However, the dissimilar substrate of the commercial product may have contributed towards its performance. The Clorox-treated substrate is very absorbent and quite fluffy, which may provide a substantial surface contact area for bacterial cells. It is postulated that the disparity in the disinfection efficacy between commercially available N-chloramine treated fabric (Clorox) and samples coated with either the Coating Formulations 1, 2 or 3 or the Coating Formulations 4, 5, 6, 7, 8 or 9 will become greater if the same substrate is used.

It was found that both of the Lululemon and Under Armour samples demonstrated significantly slower disinfection kinetics against MRSA. After 6 hours, a 3.47-log reduction was measured on the Lululemon sample and little to no killing activity was observed on the Under Armour sample, which almost overlapped with the killing kinetics of negative control of the uncoated substrate sample. Overall, the substrate samples that were coated with either of the AS1 formulation or the NC2 formulation demonstrated the most potent bactericidal efficacy, which may support using the Coating Formulations 1 through 9 in various broad applications including wound dressings, medical devices, other health care textiles and sports requisites.

Figure 11:
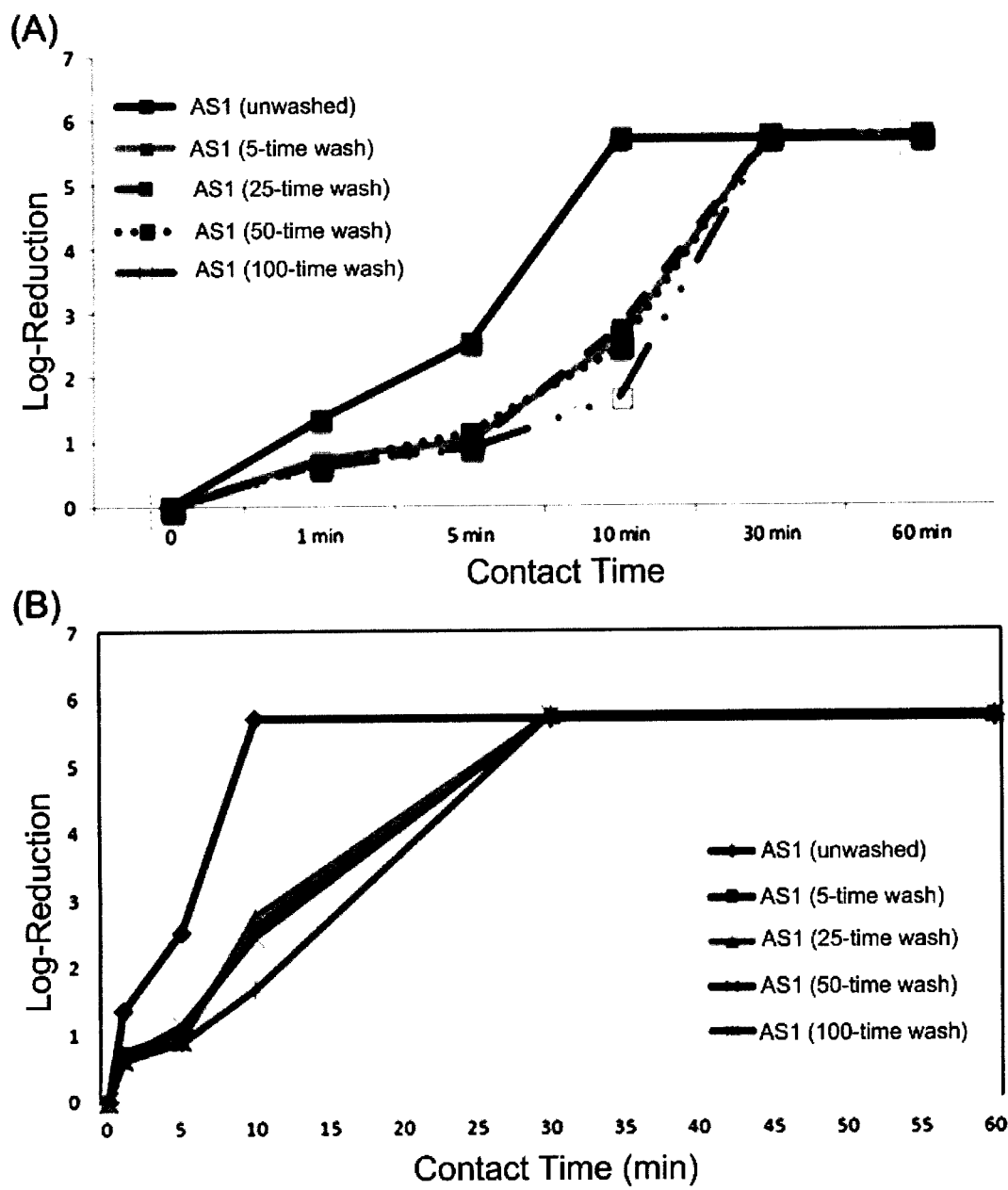
FIG. 11A and FIG. 11B are both line graphs that depict representative biocidal activity data obtained from a substrate coated in a coating formulation of the present disclosure, over time.

The ability to provide continued efficacy throughout the product life-cycle is one of the critical qualities of antimicrobial functionalized materials. The laundry durability tests of the AS1 and NC2 coated samples were conducted according to AATCC Test Method 61 (Test 2A Procedure). Washing cycles of 5, 25, 50, and 100 times were performed and then all the washed samples were then re-chlorinated at 100 ppm of chlorine. The antibacterial activities of the samples after different times of washing cycles were again evaluated against MRSA. As it can be seen in FIG. 11A and FIG. 11B, the slope of killing kinetics of the AS1 coated samples decreased immediately after 5-time wash, arriving at 1.02-log and 2.58-log reduction at 5 min and 10 min, respectively, when compared to 2.52-log and 5.70-log reduction of unwashed AS1 samples. However, there was no detectable decrease when increasing the washing cycle to 25 and 50 times, in spite of the decreased chlorine loading indicated by FIG. 9. The disinfection curves of 5-, 25-, and 50-washed AS1 samples were almost the same, achieving total kill at 30 min. Further increasing to 100-time wash resulted in a 1.67-log reduction at 10 min, slightly lower than the approximate 2.5-log reduction of the three washed samples. FIG. 11A and FIG. 11B represent the same data with different contact times provided on the x-axis.

Figure 12:
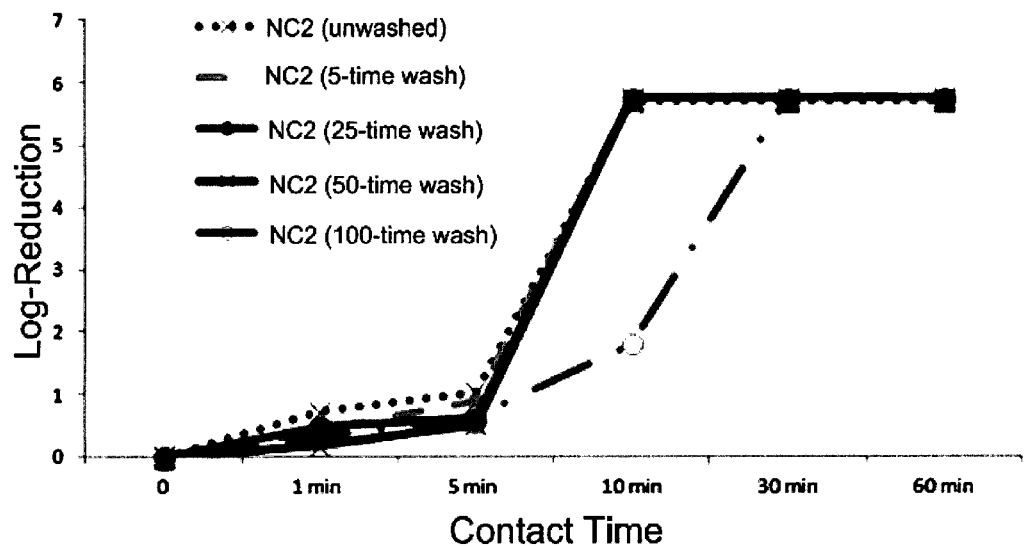
FIG. 12A and FIG. 12B are both line graphs that depict representative biocidal activity data obtained from a substrate coated in another coating formulation of the present disclosure, over time.
Figure 12:
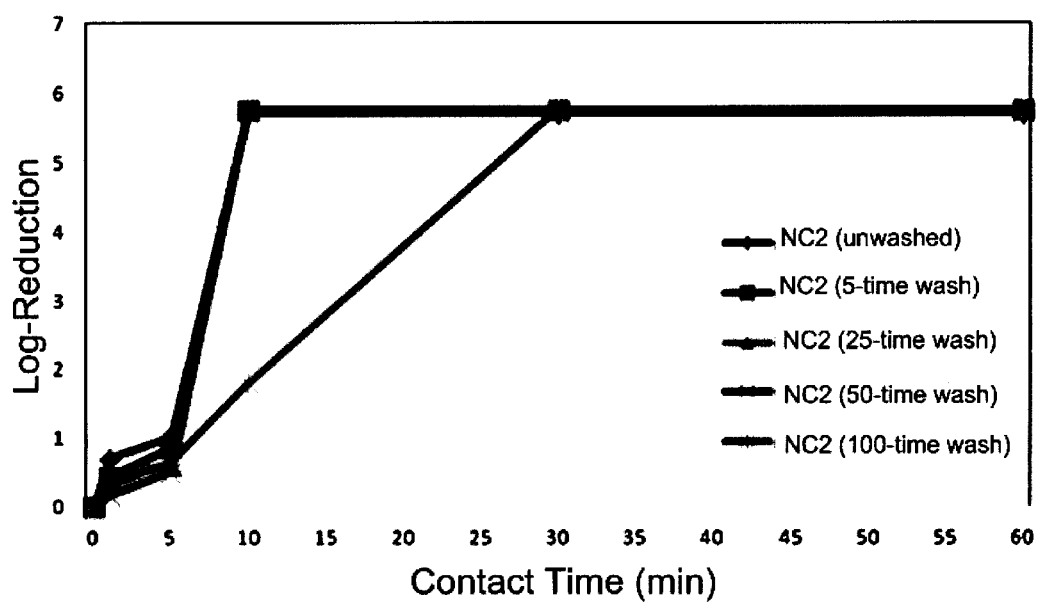

Likewise, the time-kill profiles of unwashed and washed NC2 samples are shown in FIG. 12A and FIG. 12B. No significant difference existed in the antibacterial efficiency of unwashed, 5, 25, and 50-time washed NC2 samples. All the MRSA were killed within 10 min, when compared to 1.80-log reduction of 100-time washed NC2. FIG. 12A and FIG. 12B represent the same data with different contact times provided on the x-axis.

Figure 13:
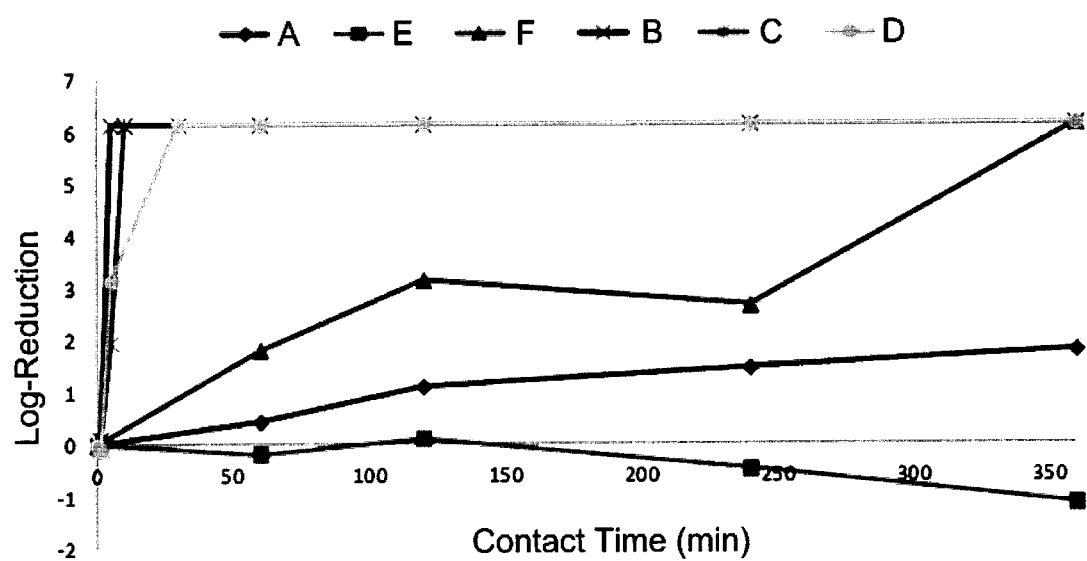
FIG. 13 is a line graph that depicts representative biocidal activity data obtained from substrates coated in coating formulations of the present disclosure and other modified textiles that were exposed to *E. coli* ATCC 25922.

FIG. 13 depicts the bacterial reduction (log) as a function of contact time between *E. coli* (ATCC 25922) and the Coated Samples. In FIG. 13 line A represents the Pristine Substrate; line B represents the AS1 coated substrate sample; line C represents the NC2 coated substrate sample; line D represents the Clorox sample; line E represents the Under Armour sample; and line F represents the Lululemon sample.

In FIG. 13, AS1 exhibited the fastest killing kinetics, arriving at 6.14-log reduction at 5 min, when compared to 1.96-log reduction of NC2 at 5 minutes. The Pristine Substrate arrived at 1.79-log reduction after 6 hours. The Under Armour sample showed minimal killing activity. It even demonstrated bacterial growth from $10^6$ CFU/mL to $10^7$ CFU/Ml after 6 hours. Lululemon with X-static Silver technology demonstrated a total killing of 6.14-log reduction at 6 hours. The Clorox sample demonstrated lower bacterial efficacy than AS1, arriving at 3.14-log reduction at 5 min, when compared to 6.14-log of AS1 and 1.96-log of NC2. Due to an experimental error, certain data have been omitted from the Clorox sample at the 10 minute point.

Generally, the biocidal activity of the samples coated with the Coating Formulation 1 of the became less effective while the samples coated with the Coating Formulation 5 was almost unaffected after 5, 25, and 50 times of washing cycles. These results coincide with the titration profiles described above. The concentration of active chlorine of AS1 samples kept decreasing along with the washing cycles, while that of NC2 samples maintained at a similar level. It indicates that NC2 possesses higher laundry durability with consistent bactericidal efficacy. No significant deviation in performance was detected between AS1 and NC2 after 100 wash cycles.

The biocidal activity of further coating formulations was tested when coated on both soft and hard substrates.

Table 61 shows a summary of biocidal activity of Coating Formulations 10, 11, 12, 15 and 16 when tested against Gram-positive MRSA bacteria.

TABLE 61

Summary of Biocidal Activity of Coating Formulations 10, 11, 12, 15 and 16.

| Bacteria | | Bacteria Reduction at various contact times (min) | | | | | |
|---|---|---|---|---|---|---|---|
| Gram-positive MRSA #40065 | SAMPLE ID | $\text{Log}_{10}$ 0 | $\text{Log}_{10}$ 1 | $\text{Log}_{10}$ 5 | $\text{Log}_{10}$ 10 | $\text{Log}_{10}$ 30 | $\text{Log}_{10}$ 60 |
| Chlorinated | F2D2P1-1 (Coating Formulation 10) | 0.00 | 0.74 | 6.13 | *2.43 | 6.13 | 6.13 |
| | F2D2P1-3 (Coating Formulation 11) | 0.00 | 1.63 | 2.04 | 6.13 | 6.13 | 6.13 |
| | F11D2P1-1 (Coating Formulation 12) | 0.00 | 1.13 | 1.55 | 6.13 | 1.52 | 1.02 |
| | F14D2P1-1 (Coating Formulation 15) | 0.00 | 1.93 | 1.96 | 6.13 | 6.13 | 6.13 |
| | F14H1P1-2 (Coating Formulation 16) | 0.00 | 2.53 | 6.13 | 6.13 | 6.13 | 6.13 |

The general trends of Table 61 were observed when these experiments were repeated.

Table 62 shows a summary of biocidal activity of Coating Formulations 17A and 18 when tested against gram positive MRSA bacteria.

TABLE 62

Summary of Biocidal Activity of Coating Formulations 17A and 18.

| Bacteria | SAMPLE ID | Bacteria Reduction at various contact times (min) | | | | | |
|---|---|---|---|---|---|---|---|
| | | $\text{Log}_{10}$ 0 | $\text{Log}_{10}$ 10 | $\text{Log}_{10}$ 20 | $\text{Log}_{10}$ 30 | $\text{Log}_{10}$ 60 | $\text{Log}_{10}$ 90 |
| | 7409WOB-F2PVP1-1 (Coating Formulation 17A) | / | −0.18 | −0.13 | 2.44 | 6.18 | 6.18 |
| | 7409WOB-F2VAP05-1 (Coating Formulation 18) | / | −0.08 | 0.71 | 2.16 | 6.18 | 6.18 |

| Unclorinated | | Bacteria Reduction at various contact times (Hours) | | | | | |
|---|---|---|---|---|---|---|---|
| Samples | | 1 hr | | 5 hrs | | | |
| Virgin Substrate | | −0.29 | 0.09 | / | / | / | / |
| 7409WOB-F2PVP1-1 (Coating Formulation 17A) | | −0.16 | 0.28 | / | / | / | / |
| 7409WOB-F2VAP05-1 (Coating Formulation 18) | | −0.14 | 0.18 | / | / | / | / |

Table 63 shows a summary of biocidal activity of Coating Formulation 22 when tested against gram positive MRSA bacteria.

TABLE 63

Summary of Biocidal Activity of Coating Formulations 22.

| Bacteria | SAMPLE ID | Bacteria Reduction at various contact times (min) | | | |
|---|---|---|---|---|---|
| | | $Log_{10}$ 0 | $Log_{10}$ 10 | $Log_{10}$ 30 | $Log_{10}$ 60 |
| Gram-Positive CA-MRSA 40065 | Unchlorinated F2V3P2-1 (Coating Formulation 22) | / | 0.47 | 0.53 | 0.47 |
| | chlorinated F2V3P2-1 (Coating Formulation 22) | / | 6.34 | 6.34 | 6.34 |

Biocidal activity analysis on Coating Formulations 31, 32 and 33 was performed and near complete bacterial killing with unchlorinated samples was observed. Without being bound by any particular theory, higher killing may be observed at earlier time periods in the chlorinated versions of these coating formulations.

Table 64 shows a summary of biocidal activity of Coating Formulations 35, 36, 37 and 38 when tested against Gram-positive MRSA bacteria.

TABLE 64

Summary of Biocidal Activity of Coating Formulations 35, 36, 37 and 38.

| | | Log-Reduction | | | | | | | |
|---|---|---|---|---|---|---|---|---|---|
| | | Contact Time (min) | | | | | | | |
| Bacteria | | 0 min | 5 min | 10 min | 30 Min | 60 min | 120 min | 240 min | 360 min |
| MRSA #40065 | AL-F2D2P1 (Coating Formulation 35 on acetal) | 1.81 | 2.35 | 4.22 | 6.24 | 6.24 | 6.24 | 6.24 | 6.24 |
| | NN-F2D2P1 (Coating Formulation 35 on nylon) | 2.20 | 2.38 | 6.24 | 6.24 | 6.24 | 6.24 | 6.24 | 6.24 |
| | NN-F2D2P5 (Coating Formulation 36) | 0.17 | 1.06 | 4.95 | 4.95 | 4.95 | 4.95 | 4.95 | 4.95 |
| | NN-F2D2P10 (Coating Formulation 37) | 0.29 | 4.95 | 4.95 | 4.95 | 4.95 | 4.95 | 4.95 | 4.95 |
| | NN-F2D2P15 (Coating Formulation 38) | 0.49 | 4.95 | 4.95 | 4.95 | 4.95 | 4.95 | 4.95 | 4.95 |

Table 65 shows a summary of biocidal activity of Coating Formulations 35, 37 and 38 when tested against Gram-positive MRSA bacteria in a chlorinated and unchlorinated state.

TABLE 65

Summary of Biocidal Activity of Coating Formulations 35, 37 and 38.

| | | Log-Reduction | | | | |
|---|---|---|---|---|---|---|
| Bacteria | | 0 mins | 5 mins | 10 mins | 30 mins | 60 mins |
| MRSA #40065 | Unchlorinated NN-F2D2P1 (Coating Formulation 35) | / | / | / | / | 0.45 |
| | Unchlorinated NN-F2D2P10 (Coating Formulation 37) | / | / | / | / | 0.17 |
| | Unchlorinated NN-F2D2P15 (Coating Formulation 38) | / | / | / | / | 0.16 |
| | NN-F2D2P1 (Coating Formulation 35) | 0.13 | 0.84 | 1.74 | 5.45 | 5.45 |
| | NN-F2D2P10 (Coating Formulation 37) | 0.41 | 5.45 | 5.45 | 5.45 | 5.45 |
| | NN-F2D2P15 (Coating Formulation 38) | 0.26 | 5.45 | 5.45 | 5.45 | 5.45 |

Table 66 shows a summary of biocidal activity of Coating Formulation 40 when tested against Gram-positive MRSA bacteria in a chlorinated and unchlorinated state.

TABLE 66

Summary of Biocidal Activity of Coating Formulation 40.

| Bacteria | Sample ID | Log Reduction at Various Contact Times (min) E. coli Inoculum 5.42-log | | |
|---|---|---|---|---|
| | | 10 | 30 | 60 |
| Gram-negative | E. coli ATCC 25922 | Control E2NAP0 | / | / | 0.67 |
| | | Unchlorinated E9PDP15-13 (Coating Formulation 40) | 1.02 | 5.42 | 5.42 |
| | | Chlorinated E9PDP15-13 (Coating Formulation 40) | 5.42 | 5.42 | 5.42 |

Accordingly, based on the foregoing, an article comprising a compound as described herein is contemplated. Monomers or precursors and polymers of the monomers, precursors and compounds are also contemplated, and articles prepared from monomers, precursors and polymers thereof are also contemplated.

Methods of inactivating a microorganism or of inhibiting microbial growth are also contemplated. A method comprising contacting the microorganism or a surface on which a microorganism resides with a compound, monomer of a compound, or an article coated with a compound or coating formulation as described herein is contemplated. The microorganism can be a bacteria, a virus or a fungus.

Other embodiments of the present disclosure relate to a method whereby a compound or an article comprising a compound described herein is exposed to a source of chlorine, bromine or iodine. In another embodiment, a method is contemplated, wherein the method comprises providing a compound or an article comprising a compound described herein and exposing the compound or article comprising the compound to a source of chlorine, bromine or iodine. The method finds use in rendering a surface aseptic or essentially aseptic. The method also finds use in recharging biocidal activity of a compound or article coated with a compound or coating formulation as described herein.

The invention claimed is:
1. A compound having a general formula that is:

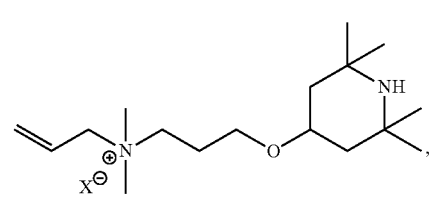
[VI]

wherein $X^-$ is $Cl^-$, $Br^-$, $I^-$ or $PO_4^{3-}$.

2. The compound of claim 1, wherein the N-halamine precursor group is converted into an N-halamine by a halogenation reaction.

3. A coating formulation comprising:
(a) a compound with the general formula:

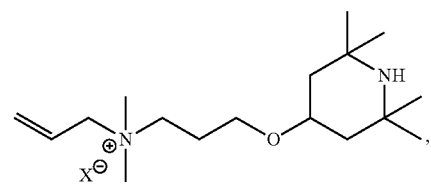
[VI]

wherein $X^-$ is $Cl^-$, $Br^-$, $I^-$ or $PO_4^{3-}$; and
(b) at least one further component that is a polymer or a component of a polymer-based system.

4. The coating formulation of claim 3, wherein the at least one further component is selected from a group consisting of: an acetate polymer; a vinyl ester polymer; a vinyl acetate polymer; a vinyl acetate homopolymer; an acrylate polymer; a methacrylate polymer; a melamine polymer; a modified melamine polymer; a urethane polymer; a polyurethane polymer; an aliphatic urethane polymer; a polyester; a self-crosslinking polyester; an epoxide polymers; an epoxide-ester polymer; a fluoropolymers; a silicone polymer; a silicone-based polymer; a polyethylene; a polypropylene; a polyvinyl chloride polymer; a polyamide polymer; a polybutylene polymer; a poly(buta-1,3-diene) polymer; a polysulfone polymer and combinations thereof.

5. A substrate with at least one surface that is coated with the coating formulation of claim 3.

6. The substrate of claim 5, wherein the at least one surface is selected from a group consisting of: a textile surface, a metal surface, a metal alloy surface, a polymer surface, a ceramic surface, a glass surface and a wood surface.

7. The substrate of claim 6, wherein the textile surface is selected from a group consisting of a natural textile, a synthetic textile and a combination thereof.

* * * * *